(12) United States Patent
Feng et al.

(10) Patent No.: US 6,890,933 B1
(45) Date of Patent: May 10, 2005

(54) KINESIN INHIBITORS

(75) Inventors: Yan Feng, Brookline, MA (US); Tarun M. Kapoor, New York, NY (US); Thomas Mayer, Brookline, MA (US); Zoltan Maliga, East Brunswick, NJ (US); Timothy J. Mitchison, Brookline, MA (US); Justin Yarrow, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/791,339

(22) Filed: Feb. 23, 2001

Related U.S. Application Data
(60) Provisional application No. 60/184,540, filed on Feb. 24, 2000.

(51) Int. Cl.[7] ..................... A61K 31/437; C02D 471/04
(52) U.S. Cl. ............................. 514/292; 546/85; 546/86
(58) Field of Search ........................... 514/292; 546/85, 546/86

(56) References Cited

U.S. PATENT DOCUMENTS
6,030,983 A * 2/2000 Behforouz et al. ......... 514/292

FOREIGN PATENT DOCUMENTS
WO        WO 00/07017        2/2000

OTHER PUBLICATIONS

Ishida, J. et al. : Antitumor agents 201. Cytotoxicity of Harmine and beta–Carboline analogs. Bioorg. & Med. Chem. Lett. vol. 9, pp. 3319–3324, 1999.*
Berge, et al., "Pharmaceutical Salts" *J. Pharmaceutical Sciences*, 66: 1–19, 1977.
Blangy, et al., "Phosphorylation by p34cdc2 Regulates Spindle Association of Human Eg5, a Kinesin–Related Motor Essential for Bipolar Spindle Formation in Vivo" *Cell*, 83: 1159, 1995.
Bloom, et al., "Cruising along microtuble highways: how membranes move through the secretory pathway" *J. Cell Biol.* 140: 1277–1280, 1998.
Cramer, et al., "Myosin is Involved in Postmitotic Cell Spreading" *J. Cell Biol.*, 131: 179–189, 1995.
Cramer, et al., "Actin–Dependent Motile Forces and Cell Motility" *Curr. Opin. Cell. Biol.* 6: 82–86, 1994.
Desai, et al., "Kin I Kinesins are Microtubule–Destabilizing Enzymes" *Cell*, 96: 69–78, 1999.
Enos, et al., "Mutation of a Gene that Encodes a Kinesin–Like Protein Blocks Nuclear Division in *A. Nidulans*" *Cell*, 60: 1019–1027, 1990.
Gallione, et al., "A Single Amino Acid Substitution in a Hydrophobic Domain Causes Temperature–Sensitive Cell–Surface Transport of a Mutant Viral Glycoprotein" *J. Virology*, 54: 374–382, 1985.

Hagan, et al., "Kinesin–related cut7 protein associates with mitotic and meiotic spindles in fission yeast" *Nature*, 356: 74–76, 1992.
Hamel, E., "Antimitotic Natural Products and Their Interactions with Tubulin", *Med. Res. Rev.* 16: 207–231, 1996.
He, et al., "A Simplified System for Generating Recombinant Adenoviruses", *Proc. Natl. Acad. Sci. USA.*, 95: 2509–2514, 1998.
Hirokawa, "Kinesin and Dynenin Superfamily Proteins and the Mechanisms of Organelle Transport" *Science*, 279: 519–526, 1998.
Hirschberg, et al., "Kinetic Analysis of Secretory Protein Traffic and Characterization of Golgi to Plasma Membrane Transport Intermediates in Living Cells" *J. Cell Biol.* 143: 1485–1503, 1998.
Hoyt, et al., "Two *Saccharomyces cerevisiae* kinesin–related gene products required for mitotic spindle assambly" *J. Cell Biol.* 118: 109–120, 1992.
Hung, et al., "Understanding and Controlling the Cell Cycle with Natural Products" *Chem. Biol.* 3: 623–639, 1996.
Hyman, et al., "Microtubule–motor activity of a yeast contromere–binding protein complex" *Nature*, 359: 533–536, 1992.
Kapoor, et al., "Allele–Specific Activators and Inhibitors for Kinesin" *Proc. Natl. Acad. Sci., U.S.A.*, 96: 9106–9111, 1999.
Kung, et al., "Preparation of Chiral, C–Protected α–Amino Aldehydes of High Optical Purity and Their Use as Condensation Components in a Linear Synthesis Strategy", *J. Am. Chem. Soc.* 121: 8401–8402, 1999.
Leonard, et al., "A One–Pot Tandem Pictet–Spengler–Diels–Alder Synthesis of Apoyohimbines From 3–Carbomethoxy–2 (Formylmethyl)–3–Sulfolene" *Tet. Lett.* 38: 3071–3074, 1997.
Lockhart, et al., "Kinetic Evidence for Low Chemical Processivity in ncd Eg5" *J. Mol. Biol.* 273: 160–170, 1997.
Mayer, et al., "Small Molecular Inhibitor of Mitotic Spindle Bipolarity Identified in a Phenotype–Based Screen" *Science*, 286: 971–974, 1999.

(Continued)

*Primary Examiner*—Charanjit S. Aulakh
(74) *Attorney, Agent, or Firm*—Brenda Herschbach Jarrell; Nadege M. Lagneau; Choate, Hall & Stewart

(57) ABSTRACT

The present invention provides for compounds, compositions, methods and systems for inhibiting cell growth. More specifically, the present invention provides for methods, compounds and compositions which are capable of inhibiting mitosis in metabolically active cells. Compounds, compositions and methods of the present invention inhibit the activity of a protein involved in the assembly and maintenance of the mitotic spindle. One class of proteins which acts on the mitotic spindle is the family of mitotic kinesins, a subset of the kinesin superfamily.

19 Claims, 15 Drawing Sheets

(1 of 15 Drawing Sheet(s) Filed in Color)

OTHER PUBLICATIONS

Rousseau, et al., "Synthesis of 3–Deaza–β–Hydroxyhistidine Derivatives and Their Use for the Preparation of Substituted Pyrrolo[2,3–c] Pyridine–5–Carboxylates via the Pictet–Spengler Reaction", *J. Org. Chem.* 63: 2731–2737, 1998.

Sakowicz, et al., "A marine natural product inhibitor of kinesin motors" *Science*, 280: 292–295, 1998.

Saunders, et al.,"Kinesin–Related Proteins Required for Structural Integrity of the Mitotic Spindle" *Cell*, 70: 451–458, 1992.

Sawin, et al., "Mitotic spindle organization by a plus–end–directed microtubule motor" *Nature*, 359: 540–543, 1992.

Sharp, et al., "The Bipolar Kinesin, KLP61F, Cross–Links Microtubules within Interpolar Microtubule Bundles of Drosophila Embryonic Mitotic Spindles",*J. Cell. Biol.*, 144: 125–138, 1999.

Steinberg, et al., "Effects of the Myosin Inhibitor 2,3–Butanedione Monoxime on the Physiology of Fission Yeast" *Eur. J. Cell. Biol.* 77: 284–293, 1998.

Stockwell, et al., "High–Throuput Screening of Small Molecules in Miniaturized Mammalian Cell–Based Assays Involving Post–Translational Modifications" *Chem. Biol.* 6(2): 71–83, 1999.

Ungemach, et al., General Method for the Assignment of Stereochemistry of 1,3–Disubstituted 1,2,3, 4–Tetrahydro–β–Carbolines by Carbon–13 Spectroscopy *J. Amer. Chem. Soc.* 102: 6976–6984, 1980.

Vale, et al., "The Design Plan of Kinesin Motors"*Annu. Rev. Cell Dev. Biol.* 13: 745–747, 1997.

Vale, et al., "Identification of a Nvel Force–Generating Protein, Kinesin, Involved in Microtubule–Based Motility" *Cell*, 42: 39–50, 1985.

Walczak, et al., "Kinesin–Related Proteins at Mitotic Spindle Poles: Function and Regulation" *Cell*, 85: 943–946, 1996.

Walczak, et al., "A Model for the Proposed Roles of Different Microtubule–Based Motor Proteins in Establishing Spindle Bipolarity" *Curr. Biol.*, 8: 903–913, 1998.

Whaley, et al., "The Preparation of 3,4–Dihydroisoquinolines and Related Compounds by the Bischler–Napieralski Reaction" *Org. Reaction.* 6:74–151, 1951.

Wood, et al., "CENP–E Is a Plus End–Directed Kinetochore Motor Required for Metaphase Chromosome Alignment", *Cell*, 91: 357–366, 1997.

* cited by examiner

Compound 22C16 fragments Golgi without affecting interphase microtubule but causes spindle defect

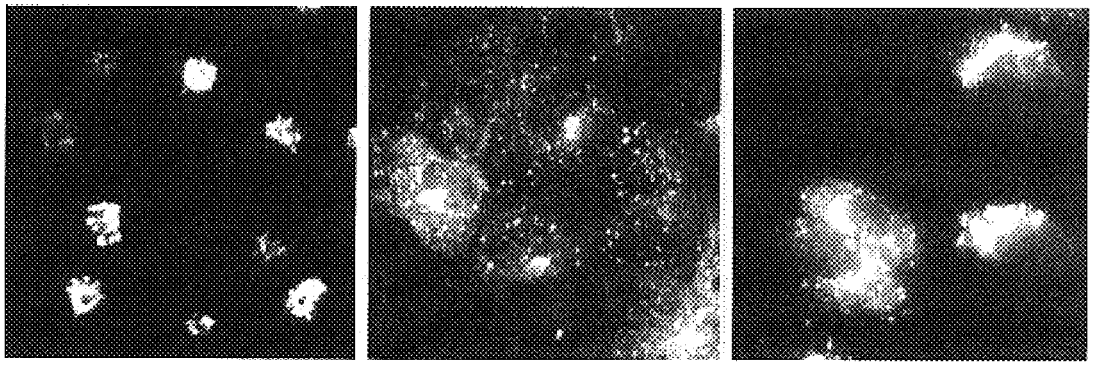

VSV-G accumulates in Golgi at 20°C (left). Upon 22C16 treatment, VSV-G accumulates in fragmented Golgi at the same condition (middle). Golgi is fragmented with 22C16 treatment as shown with GM130 staining (right).

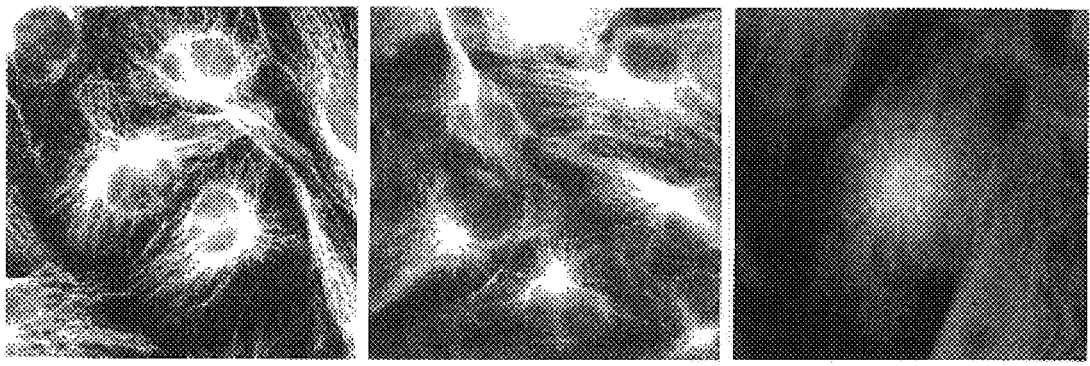

22C16 treatment does not affect interphase microtubule (left, control; middle, 22C16 treated). But monopole spindle forms upon 22C16 treatment (right, microtubule in green and chromosomes in blue).

FIG. 1

Xenopus Full length Eg5 is also inhibited by the β-carboline in vitro
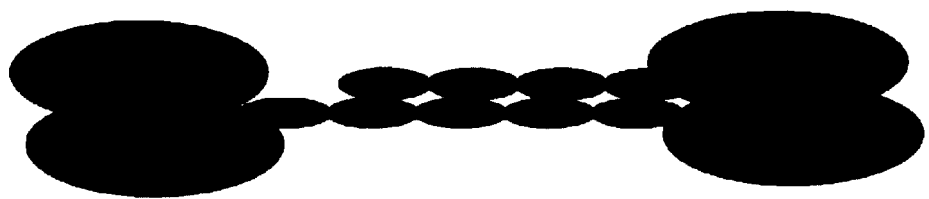
Expected Structure
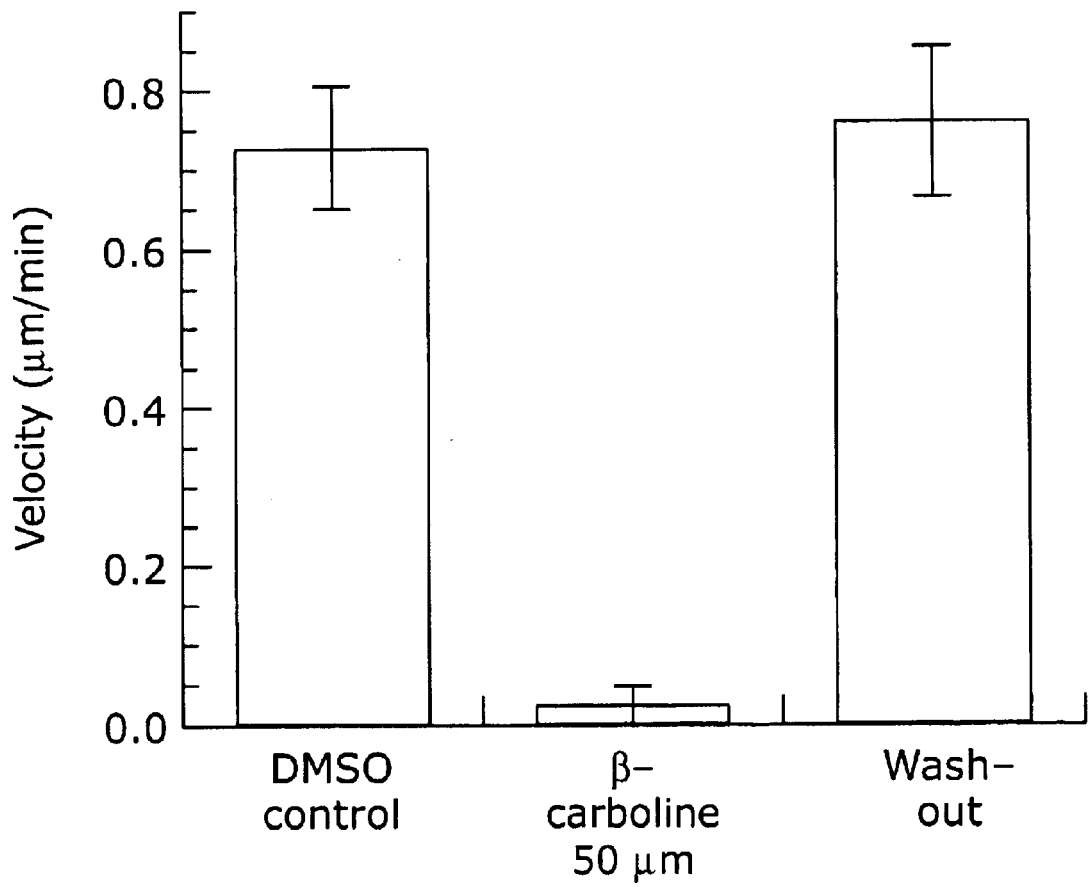
FIG. 2

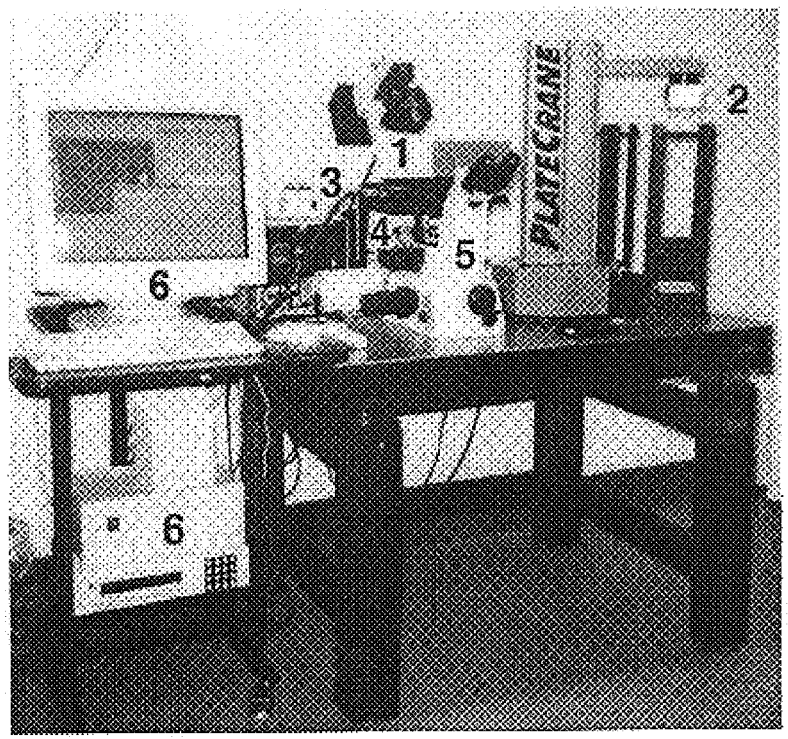
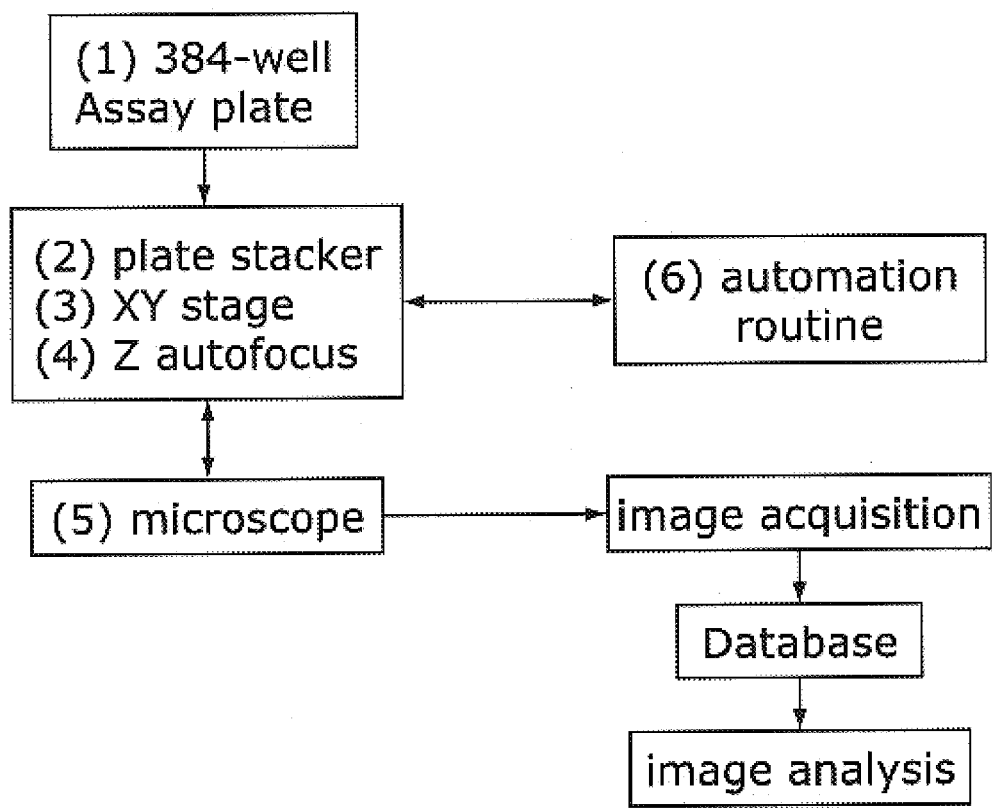
FIG. 3

NADH Enzyme Coupled Assay

In the enzyme coupled assay reaction containing LDH, PK, PEP, NADH, and ATP, one can measure the rate of ATP hydrolysis because under these reaction conditions, there is an instantaneous conversion of ADP to ATP resulting in a stoichiometric oxidation of NADH to NAD+ that can be measured as a decrease in NADH fluorescence.

Advantages:
1. Steady ATP concentration.
2. No buildup of ATP hydrolysis products that may result in feedback inhibition.
3. Many timepoints from a single reaction.

Monastroline Derivatives
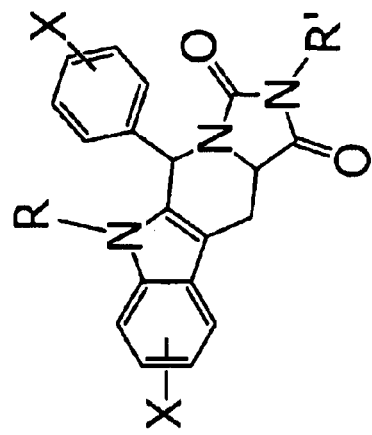
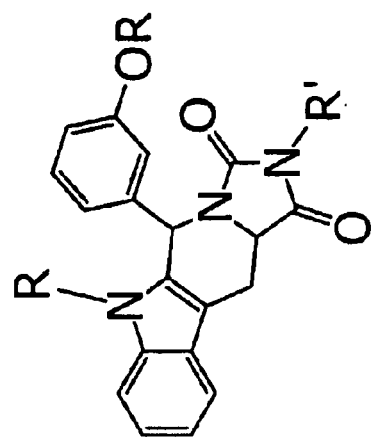
X = H, O, Cl, Br, CF$_3$, I, C
FIG. 13

KINESIN INHIBITORS

PRIORITY INFORMATION

The present application claims priority under 35 U.S.C. §119(e) to the U.S. provisional patent application Ser. No. 60/184,540 by Mitchison et al. filed on Feb. 24, 2000. U.S. Ser. No. 60/184,540 is incorporated herein by reference in its entirety.

GOVERNMENT SUPPORT

The work described in the present application was supported by a grant from the National Institutes of Health (CA78048).

BACKGROUND OF THE INVENTION

Cell-permeable small molecules can rapidly perturb the function of their targets and are therefore powerful tools to dissect dynamic cellular processes. However, such modulators are not available for most of the proteins involved in essential processes, and many of the ones that are available are nonspecific. The only known small molecules that specifically affect the mitotic machinery target tubulin (E. Hamel, Med. Res. Rev. 16, 207 (1996)), a subunit of the microtubules in the mitotic spindle.

One class of proteins involved in the assembly and maintenance of the mitotic spindle is the family of mitotic kinesins, a subset of the kinesin superfamily. This superfamily contains over 100 proteins, whose other functions include organelle transport and membrane organization (R. D. Vale and R. J. Fletterick, Annu. Rev. Cell Dev. Biol. 13, 745 (1997)). The first evidence that mitotic kinesins are important in establishing spindle bipolarity came from genetic studies: temperature-sensitive mutants in the BimC family of kinesins do not form bipolar spindles at the restrictive temperature (A. P. Enos and N. R. Morris, Cell 60, 1019 (1990); I. Hagan and M. Yanagida, Nature 356, 74 (1992); M. A. Hoyt et al., J. Cell Biol. 118, 109 (1992)). Inhibition of the BimC kinesin Eg5 with Eg5-specific antibodies also induced monoasters similar to those observed after treatment with monastrol (A. Blangy et al., Cell 83, 1159 (1995); K. E. Sawin et al., Nature 359, 540 (1992)). Like other kinesins, Eg5 can drive the movement of microtubules in vitro (T. M. Kapoor and T. J. Mitchison, Proc. Natl. Acad. Sci. U.S.A. 96, 9106 (1999)).

Enzymes in the kinesin superfamily use the free energy of ATP hydrolysis to drive intracellular movement and influence cytoskeleton organization (R. D. Vale and R. J. Fletterick, Annu. Rev. Cell. Dev. Biol. 13, 745–777 (1997)). More than 90 members of this family are known. Historically, kinesins have been proposed to move cellular cargo along polar microtubule tracks. More recently it has been shown that these ATPases can modulate dynamics of the underlying microtubule network (A. Desai et al., Cell 96, 69–78 (1999)), couple movement of cargo to the microtubule polymerization or depolymerization (K. W. Wood et al., Cell 91, 357–366 (1997)), and crosslink microtubules in dynamic structures (D. J. Sharp et al., J. Cell Biol. 144, 125–138 (1999)). Kinesins thus play central roles in mitotic and meiotic spindle formation, chromosome alignment and separation, axonal transport, endocytosis, secretion, and membrane trafficking. The cargo associated with these motor proteins includes intracellular vesicles, organelles, chromosomes, kinetochores, intermediate filaments, microtubules, and even other motors (reviewed in C. E. Walczak and T. J. Mitchison, Cell 85, 943–946 (1996); and N. Hirokawa, Science 279, 519–526 (1998)).

For many of these processes, more than one kinesin is implicated, and the specific cargo associated with a given motor protein has been difficult to establish. For example, conventional kinesin (R. D. Vale et al., Cell 42, 39–50 (1985)) (the founding member of the family) is one of a subset of kinesins involved in organelle transport in mammalian cells. This group includes KIF1, KIF2, KIFC2/C3, and KIF4; and more recently, 18 new murine KIFs have been reported, many of which may functionally overlap with the transport kinesins (reviewed in N. Hirokawa, Science 279, 519–526 (1998)). It thus has been difficult to tie down the in vivo function(s) of conventional kinesin. Experiments using antisense techniques and microinjection of inhibitory antibodies have been further complicated by recent observations of efficient endoplasmic reticulum to Golgi transport in the absence of microtubules, albeit under restricted conditions (reviewed in G. S. Bloom and L. S. Goldstein, J. Cell Biol. 140, 1277–1280 (1998)). Similar problems have been encountered in dissecting the function of kinesins in mitosis. Extensive genetic analysis of motors in Saccharomyces cerevisiae has linked all but one of the six kinesins to spindle function. None of these five motors are individually required for the viability of yeast, implying that more than one motor is associated with essential aspects of spindle movement (W. S. Saunders and M. A. Hoyt, Cell 70, 451–458 (1992); M. A. Hoyt et al., Proc. Natl. Acad Sci USA 94, 12747–12748 (1997)). Immunodepletion and add-back approaches in Xenopus extract spindle assembly assays have provided similarly ambiguous data (C. E. Walczak et al., Curr. Biol. 8, 903–913 (1998)).

Small molecules that conditionally activate or inactivate a protein are valuable tools for analyzing cellular functions of proteins (D. T. Hung et al., Chem. Biol. 3, 623–639 (1996)). Their use provides an alternative to conventional biochemical and genetic approaches. However, to date there have been few reports of small molecules that can reversibly alter the function of motor proteins. Butanedione monoxime has been used to probe the role of myosin in cell movement (L. P. Cramer and T. J. Mitchison, J. Cell Biol. 131, 179–189 (1995)), but its specificity has been questioned (G. Steinberg and J. R. McIntosh, Eur. J. Cell Biol. 77, 284–293 (1998)). A natural product inhibitor of kinesin has been reported (R. Sakowicz et al., Science 280, 292–295 (1998)), but is thought not to be selective for different kinesins and thus is not useful for probing the role of one specific kinesin in a complex process. Hyman et al. (A. A. Hyman et al., Nature (London) 359, 533–536 (1992)) have used ATP analogs to distinguish between microtubule motility at kinetochores driven by a kinesin and a dynein, but again, this approach is unlikely to distinguish between different kinesins. Thus currently there is a lack of small molecule activators or inhibitors that are specific for one member of the kinesin family. Such an inhibitory molecule with specificity for a particular member of a kinesin class would be useful as an anti-mitotic and also as an anti-cancer, anti-tumorigenic compound.

SUMMARY OF THE INVENTION

The present invention provides compounds, compositions, methods and systems for inhibiting cell growth. More specifically, the present invention provides methods, compounds and compositions that are capable of inhibiting mitosis in metabolically active cells. Compounds, and compositions of the present invention inhibit the activity of a protein involved in the assembly and maintenance of the mitotic spindle. One class of proteins which acts on the mitotic spindle is the family of mitotic kinesins, a subset of the kinesin superfamily.

In one aspect, the present invention provides a compound having the formula (I):

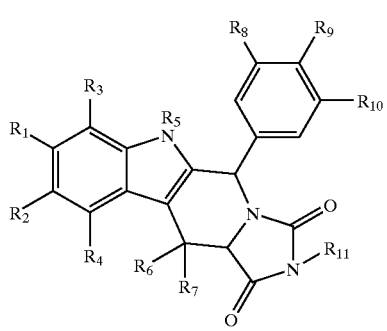

(I)

wherein $R_{1-4, 8-10}$, as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, OH, $OR_A$, $C(=O)R_A$, $CO_2H$, $CO_2R_A$, CN, halogen, SH, $SR_A$, $SOR_A$, $SO_2R_A$, $NO_2$, $NH_2$, $NHR_A$, $N(R_A)_2$, hydrogen and $NHC(O)R_A$, wherein each occurrence of $R_A$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen, and wherein $R_{5-7, 11}$ as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, $-(C=O)R_B$, and $-(SO_2)R_B$, wherein each occurrence of $R_B$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and $-(C=O)R_C$, wherein $R_C$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen.

In another aspect, the present invention provides a compound having the formula (II):

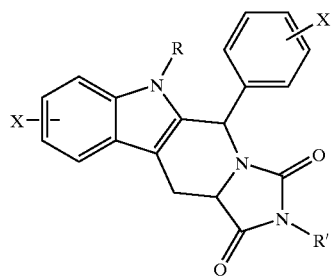

(II)

wherein X is H, O, halogen, $CF_3$, or carbon; and wherein R and R' as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, $-(C=O)R_D$, and $-(SO_2)R_D$, wherein each occurrence of $R_D$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and $-(C=O)R_E$, wherein $R_E$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen.

In yet another aspect, the present invention provides a compound having the formula (III):

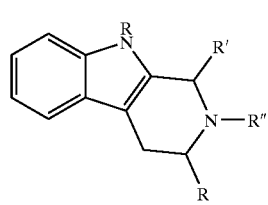

(III)

wherein R, R' and R" as as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, $-(C=O)R_F$, and $-(SO_2)R_F$, wherein each occurrence of $R_F$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and $-(C=O)R_G$, wherein $R_G$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen.

In yet another aspect, the present invention provides a compound having the formula (IV)

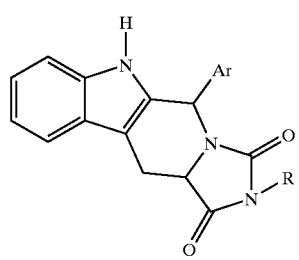

(IV)

wherein Ar is phenyl, p-hydroxyphenyl, m-hydroxyphenyl, m-methoxyphenyl, m-halogenphenyl or m-fluorophenyl and R is as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, $-(C=O)$ $R_H$, and —$(SO_2)R_H$, wherein each occurrence of $R_H$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and —$(C=O)R_I$, wherein $R_I$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen.

In still yet another aspect, the present invention provides a pharmaceutical composition comprising one or more of the compounds (I–IV) as described by the present invention and further comprising a pharmaceutically acceptable carrier.

In yet another aspect, the present invention provides a pharmaceutical composition comprising a compound having the formula (V):

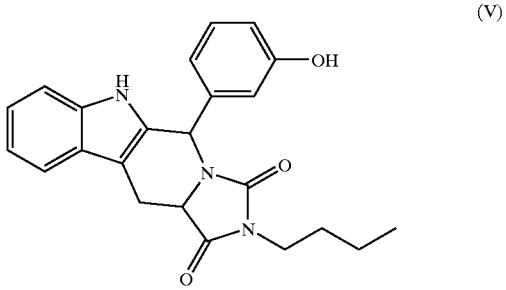

(V)

and further comprising a pharmaceutically acceptable carrier.

In yet another aspect, the present invention provides a method of treating an individual with a cancerous growth comprising administering to the individual a therapeutically effective and non-toxic dose of a composition comprising a compound having the formula (V):

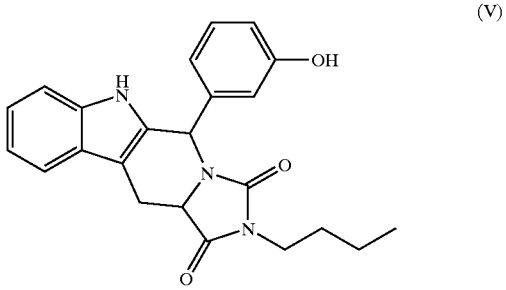

(V)

In yet another aspect, the present invention provides a method of treating an individual with a cancerous growth comprising administering to the individual a therapeutically effective and non-toxic dose of a composition comprising one or more of the compounds I–IV as described by the present invention.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 depicts the fragmentation of the Golgi and the formation of mono-astral spindles by cells treated with 22C16.

FIG. 2 depicts the results of experiments examining the motility activity of full length Xenopus Eg5 with and without the beta-carboline, 22C16. Also shown is the wash-out experiment demonstrating that 22C16 acts reversibly to inhibit the motility of Eg5.

FIG. 3 is a photograph of an automated screening microscope, with a schematic of the steps in the screening process.

FIG. 13 depicts the derivatives of monastroline where X is H, O Cl, Br, CF3, I or C.

DEFINITIONS

Figure 4:
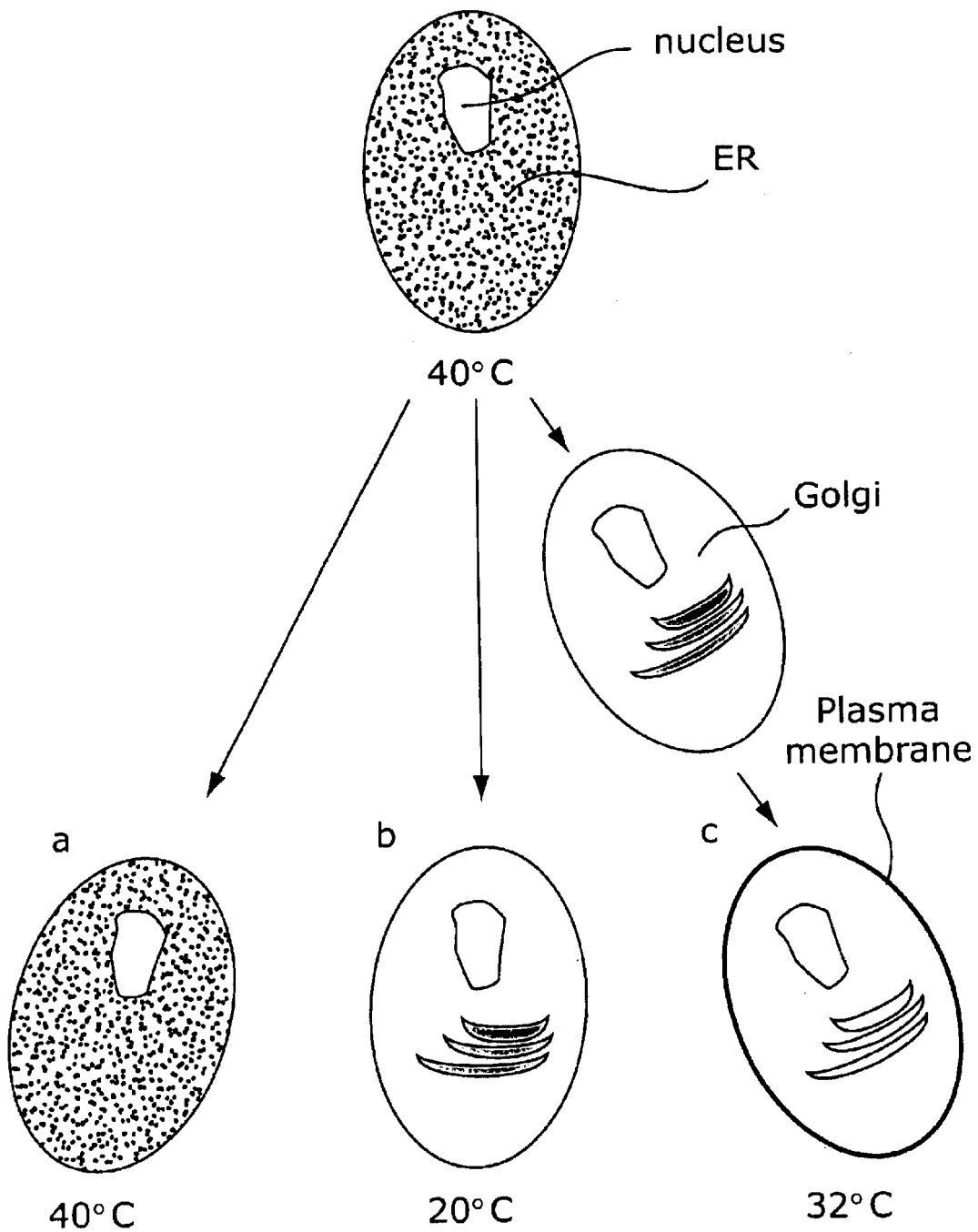
FIG. 4 is a schematic depiction of the protocol of the synchronous screen for exocytosis. The BSC1 cells were mixed with media containing the adenovirus with the VSVG-GFP construct and plated at 3,000 cells/well (~80% confluency) in a 384-well tray. After transduction, the cells were kept for 18 hours at 40° C. (the non-permissive temperature) leading to accumulation of VSVG-GFP in the ER. 50–100 nL of each chemical (in DMSO) was diluted with 40 $\mu$l of media and transferred to assay wells, followed by incubation for another hour at 40° C. The cells were then either (a) retained at 40° C. for 2 hours or incubated for 2 hours at: (b) 20° C.; or (c) 32° C. With no inhibitors present, VSVG-GFP behaves as follows: (a) retained in ER; (b) exits the ER but is retained in the trans-Golgi network; (c) exits the ER, traffics to the Golgi and continues to the plasma membrane. Traffic was ended by transferring the trays to 4° C. and fixing with 4% paraformaldehyde.

As discussed above, the present invention provides a novel class of compounds useful for the treatment of cancer and other uncontrolled cell proliferative conditions related thereto. Compounds of this invention comprise those, as set forth above and described herein, and are illustrated in part by the various classes, subgenera and species disclosed elsewhere herein.

"Therapeutically effective": As used herein, the term "therapeutically effective" is defined as an amount of a compound or composition comprising the compound which is administered to an individual in need thereof to slow or cease uncontrolled or abnormal growth of cells in the individual without toxicity.

"Cancer or cancerous growth": As used herein, the term "cancer" or "cancerous growth" means the uncontrolled, abnormal growth of cells and includes within its scope all the well known diseases that are caused by the uncontrolled and abnormal growth of cells. Non-limiting examples of common cancers include bladder cancer, breast cancer, colon cancer, endometrial cancer, head and neck cancer, lung cancer, melanoma, non-hodgkin's lymphoma, prostate cancer, and rectal cancer. A complete list of cancers is available from the National Cancer Institute (Bethesda, Md.).

It will be appreciated by one of ordinary skill in the art that numerous asymmetric centers exist in the compounds of the present invention. Thus, inventive compounds and pharmaceutical compositions thereof may be in the form of an individual enantiomer, diastereomer or geometric isomer, or may be in the form of a mixture of stereoisomers. Additionally, in certain preferred embodiments, as detailed herein, the method of the present invention provides for the stereoselective synthesis of alkaloids and analogues thereof. Thus, in certain embodiments, the compounds of the invention are enantiopure.

Additionally, the present invention provides pharmaceutically acceptable derivatives of the foregoing compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Furthermore, it will be appreciated by one of ordinary skill in the art that the synthetic methods, as described herein, utilize a variety of protecting groups. By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401–8402, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment of cancer and/or the inhibition of the growth of or the killing of cancer cells. The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes both straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups.

Unless otherwise specified, alkyl and other aliphatic groups preferably contain 1–6, or 1–3, contiguous aliphatic carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy", or "thioalkyl" as used herein refers to an alkyl group, as previously defined, attached to the parent molecular moiety through an oxygen atom or through a sulfur atom. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to methylthio, ethylthio, propylthio, isopropylthio, n-butylthio, and the like.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$–$C_3$ alkylamino groups are utilized in the present invention.

Some examples of substituents of the above-described aliphatic (and other) moieties of compounds of the invention include, but are not limited to: F, Cl, Br, I, OH, $NO_2$, CN, C(O)—alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, -alkylamino, thio, aryl-thio, heteroarylthio, benzyl-thio, alkylthio, or methylthiomethyl. Additional examples of generally applicable substituents are illustrated by the specific embodiments shown in the Examples which are described herein.

In general, the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two or three of the hydrogen atoms thereon independently with any one or more of the following moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkylamino, thio, aryl-thio, heteroarylthio, benzyl-thio, alkylthio, or methylthiomethyl. Additional examples of generally applicable substitutents are illustrated by the specific embodiments which are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted. F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkylamino, thio, aryl-thio, heteroarylthio, benzyl-thio, alkylthio, or methylthiomethyl. Additional examples of generally applicable substituents are illustrated by the specific embodiments shown in the Examples which are described herein.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be branched, unbranched or cyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzyl-thio, alkyl-thio, or methylthiomethyl. Additional examples of generally applicable substituents are illustrated by the specific embodiments shown in the Examples which are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7- membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to: F, Cl, Br, I, OH, $NO_2$, CN, C(O)-alkyl, C(O)-aryl, C(O)-heteroaryl, $CO_2$-alkyl, $CO_2$-aryl, $CO_2$-heteroaryl, $CONH_2$, CONH-alkyl, CONH-aryl, CONH-heteroaryl, OC(O)-alkyl, OC(O)-aryl, OC(O)-heteroaryl, $OCO_2$-alkyl, $OCO_2$-aryl, $OCO_2$-heteroaryl, $OCONH_2$, OCONH-alkyl, OCONH-aryl, OCONH-heteroaryl, NHC(O)-alkyl, NHC(O)-aryl, NHC(O)-heteroaryl, $NHCO_2$-alkyl, $NHCO_2$-aryl, NHCONH-heteroaryl, $SO_2$-alkyl, $SO_2$-aryl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, alkoxy, methoxymethoxy, methoxyethoxy, amino, benzylamino, arylamino, heteroarylamino, alkyl-amino, thio, aryl-thio, heteroarylthio, benzylthio, alkyl-thio, or methylthiomethyl. Additional examples of generally applicable substituents are illustrated by the specific embodiments shown in the Examples which are described herein.

Description of Certain Preferred Embodiments

The present invention provides compounds, compositions, methods and systems for inhibiting cell growth. More specifically, the present invention provides for methods, compounds and compositions which are capable of inhibiting mitosis in metabolically active cells. Compounds, compositions and methods of the present invention inhibit the activity of a protein involved in the assembly and maintenance of the mitotic spindle. One class of proteins which acts on the mitotic spindle is the family of mitotic kinesins, a subset of the kinesin superfamily.

Monastrol

Mitchison and coworkers have demonstrated that the dihydropyrimidine-based compound monastrol is capable of arresting mammalian cells in mitosis with monopolar spindles (Mayer et al. *Science* 286:971–974, 1999; incorporated herein by reference). In vitro, monastrol specifically inhibited the motility of the mitotic kinesin Eg5, a motor protein required for spindle bipolarity. Monastrol was identified as causing monoastral spindles in mitotic cells in a multistep screen. The initial screen utilized a whole-cell immunodetection assay (Stockwell et al. *Chem Biol* 1999 February; 6(2):71–83; WO 00/07017) to identify compounds that increased the phosphorylation of nucleolin. Nucleolin is a nucleolar protein that is specifically phosphorylated in cells entering mitosis, and compounds that cause mitotic arrest would be expected to have increases levels of phosphonucleolin. This initial screen identified 139 compounds from a library of 16,320 small molecules (Diverset E, Chembridge Corporation. San Diego, Calif.) as having anti-mitotic activity.

A secondary screen, utilizing an in vitro tubulin polymerization assay, ruled out molecules that target tubulin as its mode of action. Of the 139 compounds selected in the first screen, 86 compounds did not arrest mitosis by targeting tubulin and were therefore deemed interesting for further study. These 86 compounds were then tested for their effects on microtubules, actin and chromosomes. Twenty-seven of the 86 compounds had no observable effect on the microtubule and actin cytoskeleton or on chromosome distribution. Twelve of the 86 compounds had pleiotropic effects and were not evaluated further. Forty-two of the 86 compounds affected cells in interphase as well as in mitosis and thus were not specifically affecting mitosis. Cells treated with these small molecules had disorganized or partially depolymerized interphase microtubules in addition to abnormal mitotic spindle structures and misaligned chromosomes.

Five of the 86 compounds altered the mitotic spindle specifically and were thus studied further. Monastrol was identified from one of these five compounds. It was observed that monkey epithelial kidney cells (BS-C-1) treated with monastrol had abnormal mitotic spindle. The normally bipolar mitotic spindle was replaced by a monoastral microtubule array surrounded by a ring of chromosomes. Interphase cells were not affected.

In addition, by studying the effects of monastrol and a related compound DHP2 on microtubule motility, Mayer et al. (*Science* 286:971–974, 1999) determined that the inhibition of monastrol on the Eg5 kinesin is specific to monastrol. Furthermore, monastrol's inhibiting effect on motility is specific for the Eg5 kinesin. Monastrol did not inhibit microtubule motility driven by conventional kinesin (Mayer et al. *Science* 286:971–974, 1999.)

Monastroline

It is an aspect of the present invention that a compound (and pharmaceutical compositions comprising the compound) having the formula (I) arrests cells in mitosis and therefore inhibits cell growth. The compound, a β-carboline class compound, is designated as 22C16 from the Diverset E library of small molecules (Chembridge Corporation) and is also referred to herein as monastroline.

Figure 14:
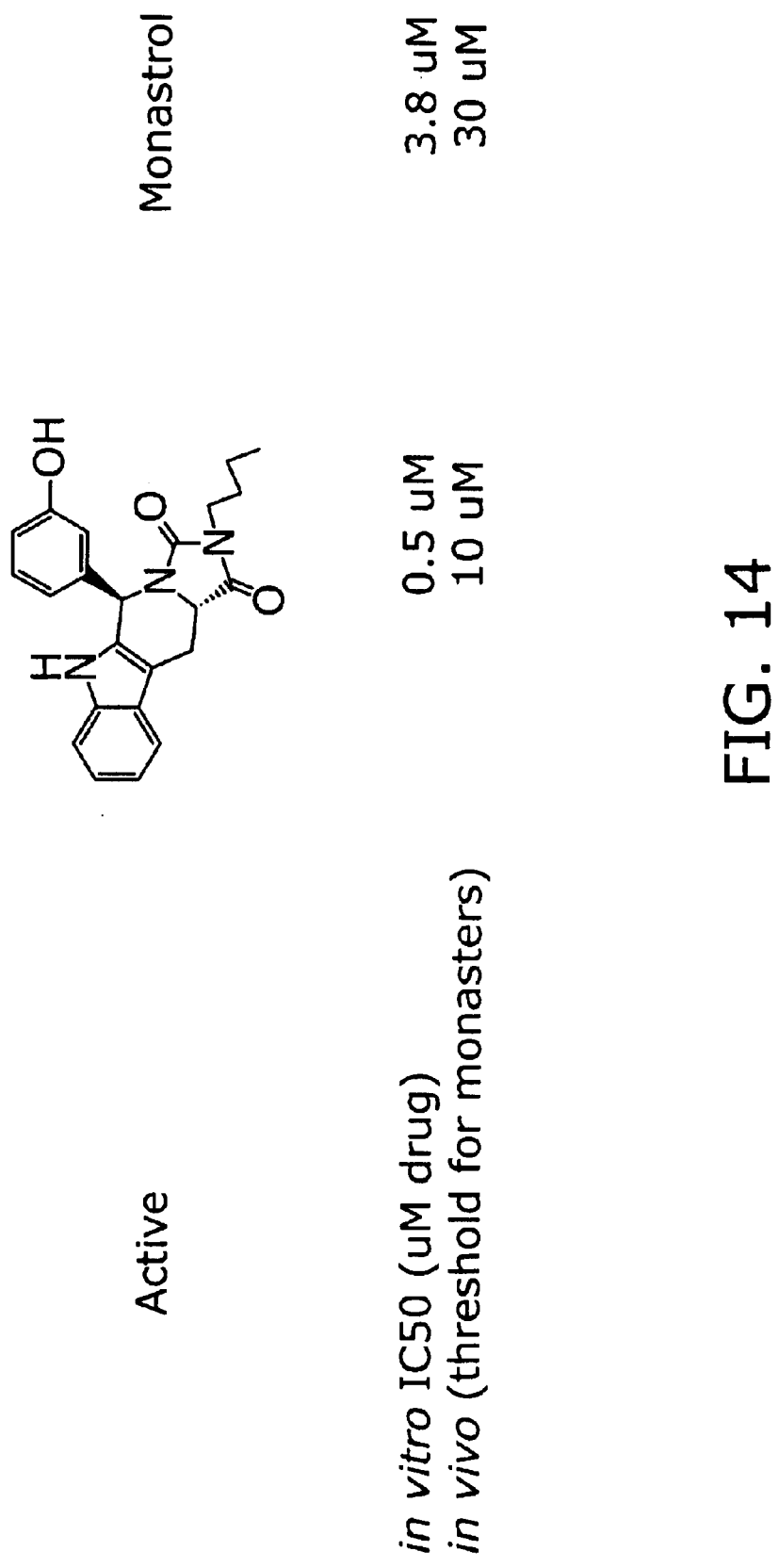
FIG. 14 depicts the structure of a trans isomer of monastroline which has an IC50 approximately 8 times lower than for monastrol as assay by the ATPase assay described in Example 2.

It is readily appreciated by one skilled in the art that the compound designated as 22C16 structure (depicted by the structural formula (V)) contains two chiral centers and that the four stereoisomers of 22C16 are encompassed by the description of the present invention. Experiments on an optically purified stereoisomer showed that a trans isomer of 22C16 shown in FIG. 14 has an IC50 which is approximately 8 times lower than monastrol.

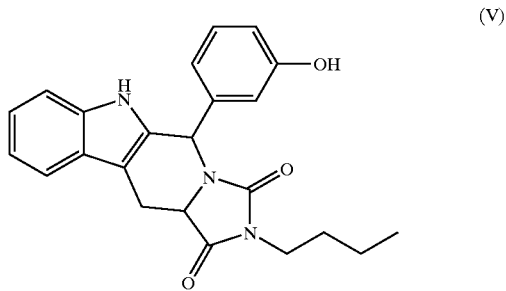

(V)

The present invention teaches that monastroline affects the mitotic machinery of mammalian cells by inhibiting the mitotic activity of a kinesin. More specifically, 22C16 is capable of inhibiting the ATPase activity of the human mitotic kinesin Eg5. As previously described, enzymes in the kinesin family use the free energy of ATP hydrolysis to drive intracellular movement and effect cytoskeleton structure. Example 2 describes experiments demonstrating that 22C16 inhibits the ATPase activity of a mitotic kinesin. These experiments utilized a purified recombinant human kinesin, Eg5.

In addition, 22C16 is capable of arresting cells in mitosis. It was observed that 22C16 affected the spindles of mitotic mammalian cells in a manner similar to that observed for monastrol (Mayer et al. *Science* 286:971–974, 1999). Monastrol causes the spindles in mitotic mammalian cells to form a mono-astral microtubule array surrounded by a ring of chromosomes. This phenotype was also observed when 22C16 was added to monkey-derived BSC1 cells (see Example 1 and FIG. 1).

In experiments studying the secretion of a viral G protein, approximately 140 compounds from the Diverset E library of small molecules (Chembridge Corp.) were found to affect the transport of a temperature sensitive mutant of a viral G protein fused to a green fluorescent protein (GFP). More importantly, 42 of the 140 compounds were found to affect the Golgi of the cells resulting in a fragmented Golgi phenotype. During the analysis of these 42 compounds for their effects on Golgi fragmentation and microtubule structure, it was observed that one compound, 22C16, fragmented the Golgi without affecting interphase microtubules. In addition, 22C16 caused a spindle defect similar to that observed for monostral (FIG. 1). 22C16 causes spindles in mitotic mammalian cells to form a mono-astral microtubule array surrounded by a ring of chromosomes.

When the effects of 22C16 and monastrol on microtubule structure were directly compared, it was shown by examining formation of mono-astral structures that 22C16 has an IC50 (median inhibitory concentration) of approximately 2 uM as compared to the IC50 of approximately 20 uM for monastrol (Mayer and Mitchison, unpublished observations). For experimental details on the cell assay to determine mono-astral structures, see Mayer et al. *Science* 286:971–974, 1999. Images of live BS-C-1 cells were taken as described (Cramer et al. *Curr. Opin. Cell. Biol.* 67:82, 1994). Briefly, for immunofluorescence, BS-C-1 cells were stained with DAPI (4',6-diamidino-2-phenylindole; Sigma-Aldrich) to visualize DNA and anti-α-tubulin (DM1 A; Sigma-Aldrich, St. Louis) to visualize spindle structure.

Since the effect of 22C16 on mono-astral formation in mammalian cells was similar to that of cells treated with monastrol, the ability of 22C16 to inhibit kinesins was examined. Example 2 describes experiments demonstrating that 22C16 specifically affects the ability of the Eg5 kinesin to hydrolyze ATP. It was shown that 22C16 inhibits the ability of Eg5, but not conventional human kinesin, to hydrolyze ATP in the presence of NADH and microtubules.

In addition, the ability of 22C16 to inhibit microtubule motility driven by Eg5 was examined. For experimental protocols and details, see Mayer et al. *Science* 286:971–974, 1999. Full length Xenopus Eg5 was expressed in baculovirus according to standard protocols (see Coligan et al. *Current Protocols in Protein Science* and Ausubel et al. *Current Protocols in Molecular Biology.* John Wiley & Sons. Incorporated herein by reference.) FIG. 2 shows that 22C16 reversibly inhibits microtubule motility driven by full-length Eg5. For the washout, Eg5-driven microtubule motility in the presence of 22C16 was measured. The assay chamber was then depleted of 22C16 and motility was immediately measured again. Therefore, the results of the experiment depicted in FIG. 2 provide direct evidence that 22C16 inhibits the microtubule motility driven by Eg5.

Uses

Any system where the control of cellular growth and cell division is desired may utilize compounds in the beta-carboline class to regulate mitosis. More specifically, in a preferred embodiment, the compound previously designated and described as 22C16 may be used to inhibit cell growth. One non-limiting example of an application of 22C16 to a cellular system is the use of 22C16 as an anti-mitotic anti-cancer drug. Other examples include controlling cell division and the immune system in diseases such as rheumatoid arthritis.

In a preferred embodiment, a method of treating an individual with uncontrolled or abnormal cell growth is provided. Compositions comprising monastroline or derivatives with similar biological activity are useful for treating individuals with cells that having become cancerous tumors. As discussed monstroline and derivatives with similar structure and biological activity are provided, preferably in as pharmaceutical composition containing a pharmaceutically acceptable carrier. The compositions containing monstroline and/or derivatives can be administered to an individual in need thereof at therapeutically effective amounts to slow or cease the abnormal cell growth. Generally, abnormal cell growth is associated with cancerous cells. However, other diseases resulting from uncontrolled cell growth (e.g. cardiovascular diseases, rheumatoid arthritis etc.) may be treated with compositions and methods of the present invention.

Pharmaceutical Compositions

As discussed above, unexpectedly, the present invention provides novel compounds having antitumor and anti-cell proliferative activity, and thus the inventive compounds are useful for the treatment of cancer. Accordingly, in another aspect of the present invention, pharmaceutical compositions are provided, wherein these compositions comprise any one of the compounds as described herein, and optionally comprise a pharmaceutically acceptable carrier.

In certain preferred embodiments, these compositions optionally further comprise one or more additional therapeutic agents. In certain other embodiments, the additional therapeutic agent is an anticancer agent, as discussed in more detail herein. It will also be appreciated that certain of the compounds of present invention can exist in free form for treatment, or where appropriate, as a pharmaceutically acceptable derivative thereof According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesiurn, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, according to the methods of treatment of the present invention, tumor cells are killed, or their growth is inhibited by contacting said tumor cells with an inventive compound or composition, as described herein. Thus, in still another aspect of the invention, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result.

In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors and also kill and/or inhibit the growth of multidrug resistant cells (MDR cells).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, y-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and the equivalents thereof.

EXAMPLE 1

Screen to Identify Small Molecule Inhibitors of Exocytosis Automated Image Capture Automated screening microscope was developed to allow medium-throughput imaging-based screening. A Nikon inverted fluorescence microscope equipped with a 20× dry lens (F 0.45) was equipped with a cooled charged coupled device (CCD) camera and the Metamorph software suite (Universal Imaging Corp.) for data acquisition. Changes in the focal plane were obtained by controlling the focal length of the optical path with a piezo-electric collar attached to the 20× dry lens with steps of 5 $\mu$m on a total range of 300 $\mu$m. Best focus was achieved by using an algorithm that searches for maximum contrast on the acquired image. The microscope set-up is diagrammed in FIG. 3.

The Metamorph Software Performs the Following Tasks:
(1) automatically center the lens in each well of a tissue culture plate (in our case, 384-well plates);
(2) automatically focus the image, by collecting 25 images in different focal planes and identifying the image with maximum contrast; and
(3) transfer the final in-focus image (642 kilobytes) to the hard drive of the attached computer (Pentium III, 1 Gigabyte RAM, 28 Gigabyte hard drive).

On average, data were collected from 20–40 cells per field. Complete data acquisition for a 384-well tray was accomplished in approximately one hour. The typical memory requirement for a screen of 10,000 compounds is approximately 6 Gigabytes.

Implementation of the Synchronous Screen for Exocytosis

VSVG-ts045 (Gallione and Rose, J. Virology 54:374–82. 1985) is a temperature sensitive mutant of the G protein of VSV (vesicular stomatitis virus) that is retained in the ER if the cells are grown at the non-permissive temperature of 40° C. When cells are transferred to the permissive temperature of 32° C., VSVG-ts045 exits the ER and continues its traffic through the Golgi complex, finally reaching the plasma membrane. Others have shown that it is possible to add the green fluorescence protein (GFP) to the cytoplasmic tail of VSVG-ts045 (abbreviated here as VSVG-GFP), and that this chimera traffics in a similar way (Hirschberg et al., *J. Cell Biol.* 143:1485–1503. 1998).

Figure 5A:
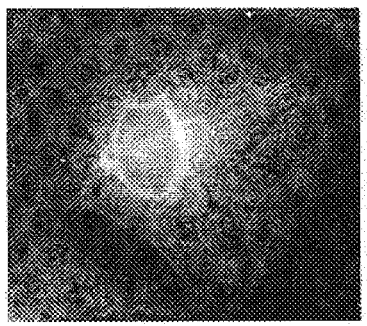
FIG. 5 shows the intracellular localization of VSVG-GFP along the secretory pathway. These images demonstrate (a) the retention of VSVG-GFP in the ER in cells kept at 40° C. The ER appears as a reticulum throughout the cell. (b) Retention of VSVG-GFP in the perinuclear regions corresponding to the Golgi complex in cells incubated at 20° C; and (c) Accumulation of VSVG-GFP at the plasma membrane, following exit from the ER and traffic through the Golgi in cells incubated at 32° C.
Figure 5B:
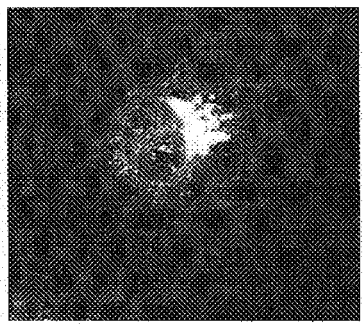
Figure 5C:
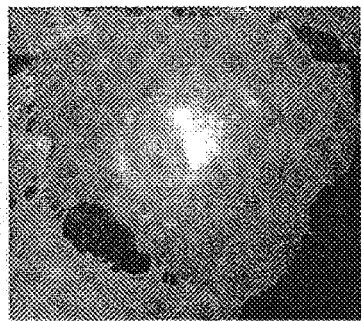

We generated a construct of VSVG-GFP and inserted it into an adenovirus-based expression vector (He et al., Proc. Natl. Acad. Sci. USA 95:2509–2514. 1998). The adenovirus containing the construct was amplified in COS cells and aliquots of the media were used for transduction in monkey-derived BSC1 cells. Almost 100% of the cells express high amounts of VSVG-GFP that can be detected by fluorescence microscopy 18 hours after infection. The protocol used in the screen for exocytosis is shown in FIG. 4; an example of the type of images that are acquired in the absence of added compounds is shown in FIG. 5.

Figure 6:
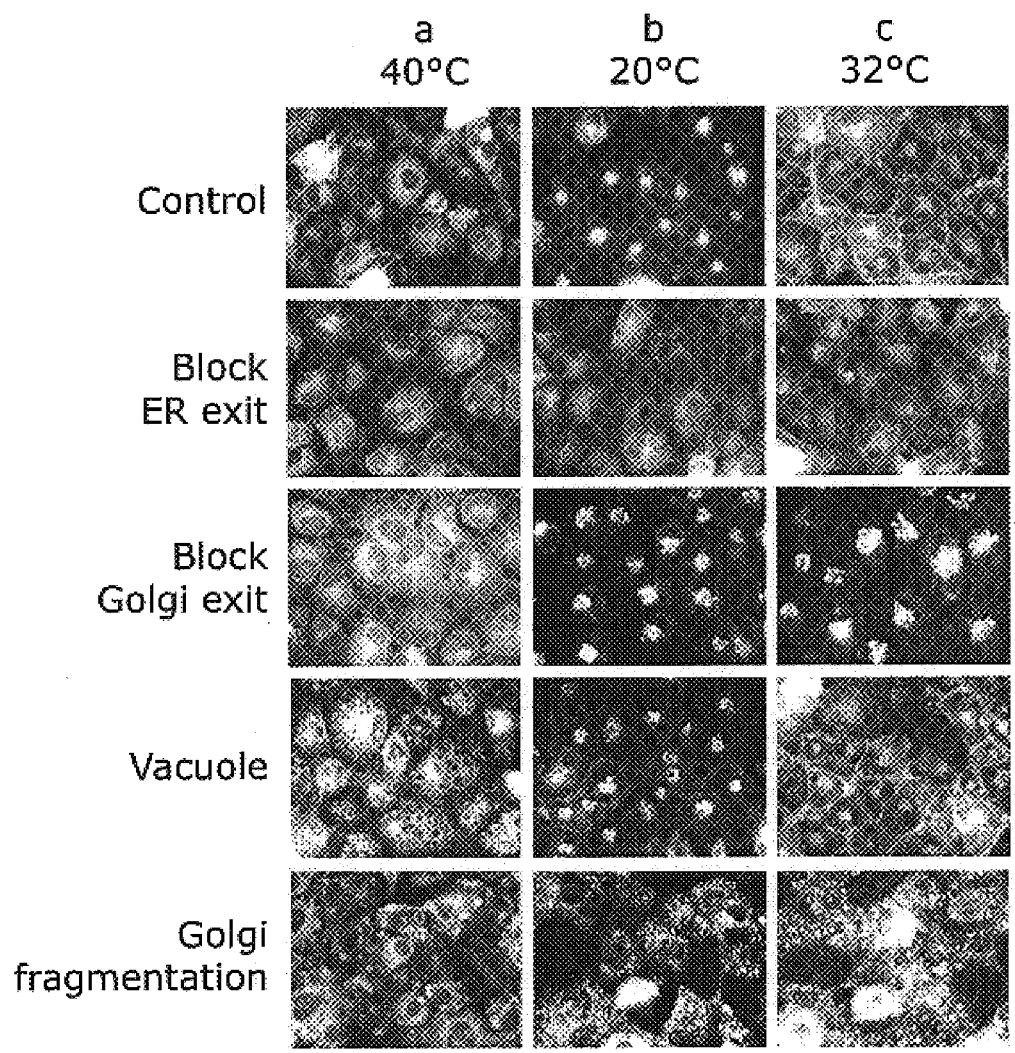
FIG. 6 shows images of cells with disruption in membrane traffic of VSVG-GFP due to various hits. These images are typical examples of the type of disruptions observed during the primary screen induced by the chemicals following the protocol summarized in FIG. 4. To facilitate the presentation of the data, we only show ¼ of the complete field.

The images were retrieved using Metamorph, and scored for variations in the pattern of VSVG-GFP traffic by direct visual inspection. Images were classified into one of several phenotypes, as shown in FIG. 6.

Summary of the Exocytic Screen

We tested the effect of ~10,000 compounds (out of a total of 16,320) from the Chembridge collection (Diverset E; Chembridge Corporation) in the traffic of VSVG-GFP following the protocol described above. About 140 hits were founds with obvious effects on single steps in the traffic properties of VSVG-GFP (FIG. 6). Twenty-six hits that act at nominal concentrations of 100 $\mu$M or lower (based on dilutions of stock solutions) were selected for further study. A summary of this stage of the screen is given in Table 1.

We next used a suite of secondary screens to explore how extensive the effects of these chemicals are on treated cells. This secondary screen consisted of tests for (a) perturbations in the intracellular organization of the tubulin-based cytoskeleton; (b) variations in the intracellular distribution of ER, Golgi and lysosomal markers; and (c) changes in the rate of uptake and intracellular targeting to endosomes of Texas Red transferrin internalized by receptor-mediated endocytosis.

It was observed in the primary screen described that one compound 22C16 fragmented the Golgi of treated mammalian cells. However, 22C16 did not depolymerize interphase microtubules and in fact, caused the formation of monopolar spindles in mitotic cells. FIG. 1 shows the effects of 22C16 on Golgi fragmentation and spindle structure. As viewed in the lower right panel of FIG. 1, 22C16 causes the formation of monospindles with a mono-astral microtubule array surrounded by a ring of chromosomes.

The observation of a mono-astral phenotype in mitotic cells treated with 22C16 led to experiments to study the effects of 22C16 on Eg5 as was previously performed with monastrol (Mayer et al. *Science* 286:971–974, 1999). The motility assay of 22C16 on Eg5 was described in the preferred embodiments of this application and the data are depicted in FIG. 2. The direct comparison of 22C16 and monastrol on the monopolar spindle mono-astral formation on mammalians was also described in the preferred embodiments.

EXAMPLE 2

ATPase Assay with Purified Human Eg5 Kinesin

Monastrol and 22C16 were both determined to block the ATPase activity of human Eg5 (N-terminal 405 amino acids and 6-His tagged at C terminus). Monastrol did not inhibit the activity of human kinesin (N-terminal 560 amino acids of full length protein followed by 6-His tag at C terminus).

Methods

Preparation of Recombinant Human Eg5 Kinesin (Eg5-405)

DNA encoding full length human Eg5 kinesin was amplified by the polymerase chain reaction (PCR) using Vent DNA polymerase (NE Biolabs, Beverly, Mass.) and subcloned into an expression plasmid (pRSETa). For the PCR reaction, the template used was a pBluescript vector containing the full length coding sequence for human Eg5 (a gift from Anne Blangy). The 5' primer (5'-GCA ACG ATT AAT ATG GCG TCG CAG CCA AAT TCG TCT GCG AAG) contained an Ase I cleavage site upstream of the Eg5 start codon. The 3' primer (5'-GCA ACG CTC GAG TCA GTG ATG ATG GTG GTG ATG CAT GAC TCT AAA ATT TTC TTC AGA AAT) was complimentary to amino acid 405 and added a downstream six histidine tag (6-HIS) followed by a UGA stop codon, and Xho I cleavage site.

The resulting PCR DNA amplification product and also the target plasmid to be used as the expression plasmid (pRSETa) were double digested with Ase I/Xho I and Nde I/Xho I respectively (New England Biolabs). Both products of the two restriction enzyme double digests were resolved and purified by agarose gel electrophoresis. The bands on the agarose gel corresponding to the desired DNA fragments, more than 2 kb for pRSETa and 1.2 kb for Eg5-405 were excised and purified (Qiagen Gel Purification Kit). The cleaved and purified DNA fragments were ligated together using T4 DNA ligase (New England Biolabs). The ligation products were transformed into E. coli DH5α chemically competent cells (Life Technologies), and selected by overnight growth on LB ampicillin plates. Transformants were amplified by growth of E. coli in LB ampicillin. Plasmids were purified (Qiagen Midiprep), and sequenced (Harvard Medical School Biopolymer Facilities).

Purification of Eg5-405 and K560 (560 Amino Acid Kinesin Construct):

BL21 pLysS (DE3) bacteria were transfected with the expression plasmid described in the preceding section and grown overnight at 37° C. on LB plates containing 100 ug/ml ampicillin (LB-amp). Several colonies were picked and grown at 37° C. in 1 ml LB-amp, pooled and used to inoculate each of six 1.5 L of LB-amp. These 1 L cultures were incubated at 37° C. on a shaker (200 RPM) until the optical density (O.D.) of the culture reached an absorbance of approximately $A_{600\ nM}=0.5$ O.D. The cultures were cooled to 20° C., induced with 24 mg/ml of isopropyl beta-D-thiogalactopyranoside (IPTG; Boehringer Mannheim) and incubated at room temperature for approximately 3 hours. Cells were pelleted by centrifugation (4000× g), rinsed in phosphate buffered saline (PBS) and repelleted at 10,000×g). The bacterial pellets were flash frozen in liquid nitrogen and stored at −80° C.

The bacterial pellets were thawed on ice and resuspended in a solution containing 50 mM potassium phosphate (pH 8.0), 250 mM KCl, 0.1% Tween-20, 10 mM imidazole, 0.5 mM magnesium adenosine triphosphate (Mg-ATP), 1 mM phenylmethanesulfonyl fluoride (PMSF), and 2 mM benzimidine-HCl. To lyse the bacteria, lysozyme (1 mg/ml) and 2-mercaptoethanol (5 mM) were added to the solution to result in the indicated final concentration, incubated and sonicated (3 times 20 seconds, repeated 3 times incubating for 1 minute on ice between each triple sonication) to break up the DNA and guarantee bacterial lysis.

The lysate was spun at 40,000×g for approximately 35 minutes at 4° C. with the resulting supernatant separated from the pellet by decanting and then incubated with a nickel-nitrilotriacetic acid resin (Ni-NTA; QIAGEN). The remaining pellet was washed three times with a wash buffer (lysis buffer supplemented with 10 mM 2-mercaptoethanol, no PMSF, and 0.1 mM Mg-ATP) to extract any remaining protein. These washes were then followed by a final wash using a low pH buffer (pH 6.0). The wash solutions were then also added to the Ni-NTA resin. The resin containing the desired tagged protein was poured into a column (Biorad, 0.8×4 cm PolyPrep Chromatography Column) and allowed to settle. The HIS-tagged proteins were eluted with a solution containing 250 mM imidazole and 150 mM KCl (pH 7.0). Protein-containing fractions of the eluate were loaded onto a Superose 6 size-exclusion column (Pharmacia) and equilibrated with a solution containing 80 mM potassium HEPES (pH 6.8), 200 mM KCl, 10 uM Mg-ATP, 1 mM dithiothreitol (DTT). Fractions containing homogeneous proteins as determined by molecular weight and mobility on SDS-PAGE were used for further enzymology experiments.

Polymerization of Microtubules:

A solution containing 1 mg/ml tubulin, 1 mM DTT, 1 mM guanosine triphosphate (GTP), 1 mM $MgCl_2$, 80 mM potassium HEPES (pH 6.8), and 1 mM ethylene glycol-bis(beta-aminoethyl ether)-N,N,N'N'-tetraacetic acid (EGTA) was spun at 90,000×g for 5 minutes. The solution was then warmed to 37° C. for 2 minutes. Taxol was added in stepwise as 0.01, 0.1, and 1 equivalents. The polymerization solution was placed onto a solution containing 40% glycerol, 80 mM potassium HEPES (pH 6.8), 1 mM $MgCl_2$, and 1 mM EGTA, and centrifuged at 90,000×g for approximately 50 minutes. The resulting microtubule pellet was washed extensively with and resuspended in resuspension buffer containing 80 mM potassium HEPES (pH 6.8), 1 mM $MgCl_2$, and 1 mM EGTA.

In vitro NADH Enzyme Coupled A TPase: (variation on Methods Described in Crevel, Lockhart, and Cross. *J. Mol. Biol.* (1997) 273, 160–170.)

Figure 7A:
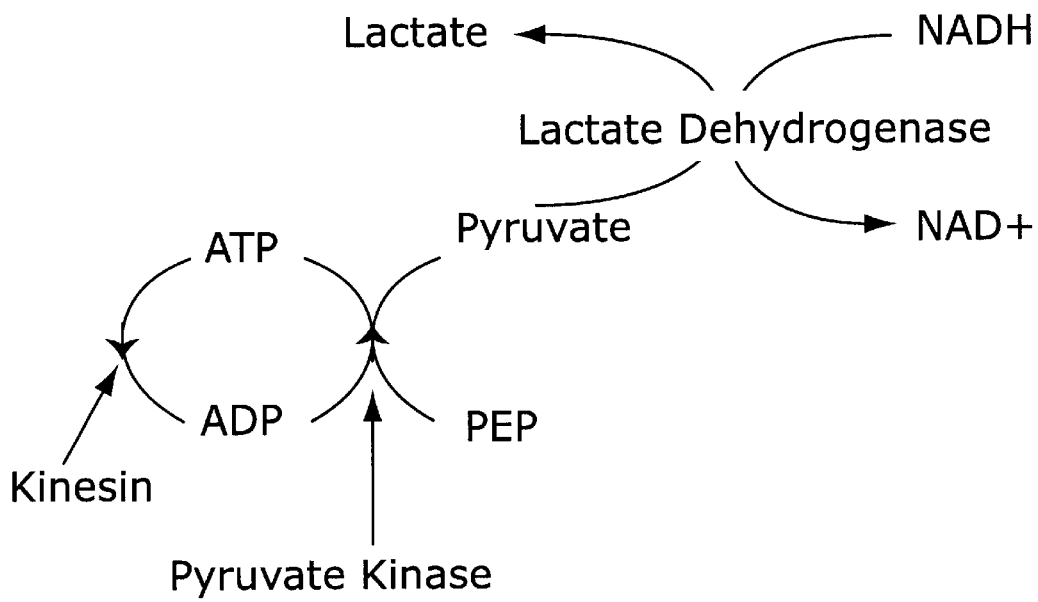
FIG. 7 depicts a description of the NADH enzyme coupled ATPase assay used to study the inhibition of the ability of purified human recombinant Eg5 to hydrolyze ATP in the presence and absence of 22C16 and monastrol.
Figure 7B:
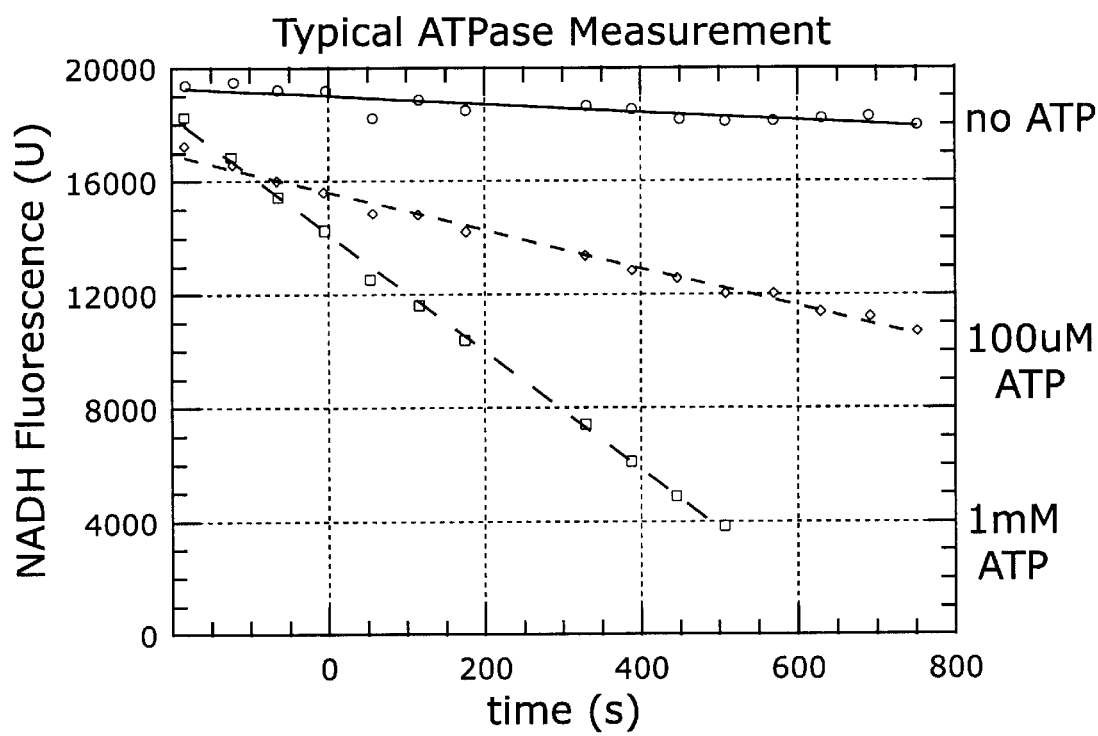

For a brief description as the ATPase assay used in the present example, see FIG. 7.

A solution containing the microtubule resuspension buffer was supplemented with 1 mM Mg-ATP, 100 uM nicotinamide adenine dinucleotide (NADH), 1 mM phosphoenol pyruvate, 5 ug/ml pyruvate kinase, 7.5 ug/ml lactate dehydrogenase, 0.7 uM resuspended microtubules, and 0.5% dimethylsulfoxide (DMSO).

Next, serial dilutions of the compound 22C16 were prepared in the supplemented microtubule resuspension buffer. Purified recombinant human Eg5 protein was added resulting in a final concentration of 50 uM. The subsequent fluorescent reaction was measured in NUNC black walled 384 well plates at 340 nm using a Wallac plate reader.

Figure 8:
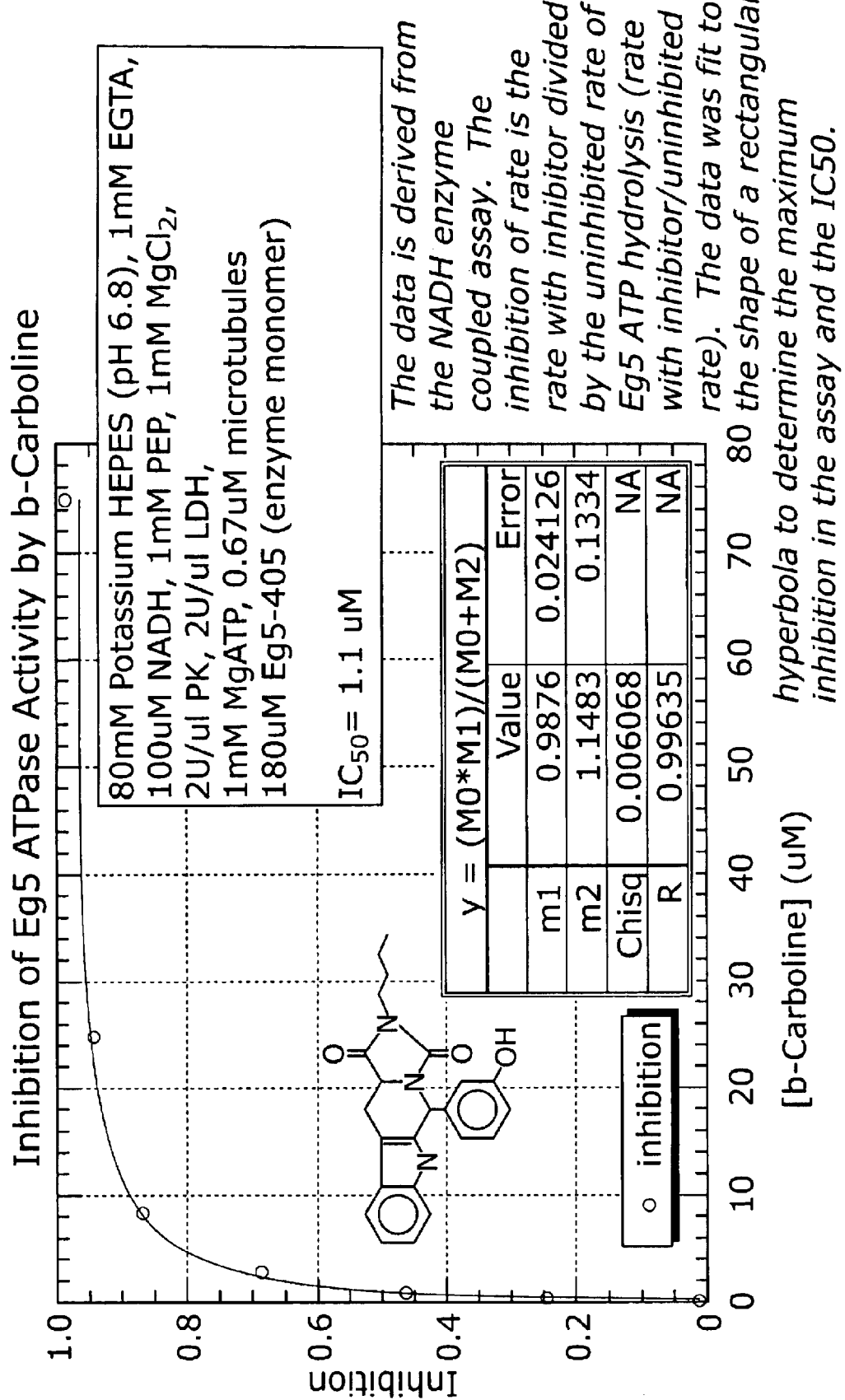
FIG. 8 depicts data from an experiment examining the inhibition of Eg5 ATPase activity by the beta-carboline, 22C16. As indicated, the IC50 for this experiment is 1.1 uM.
Figure 9:
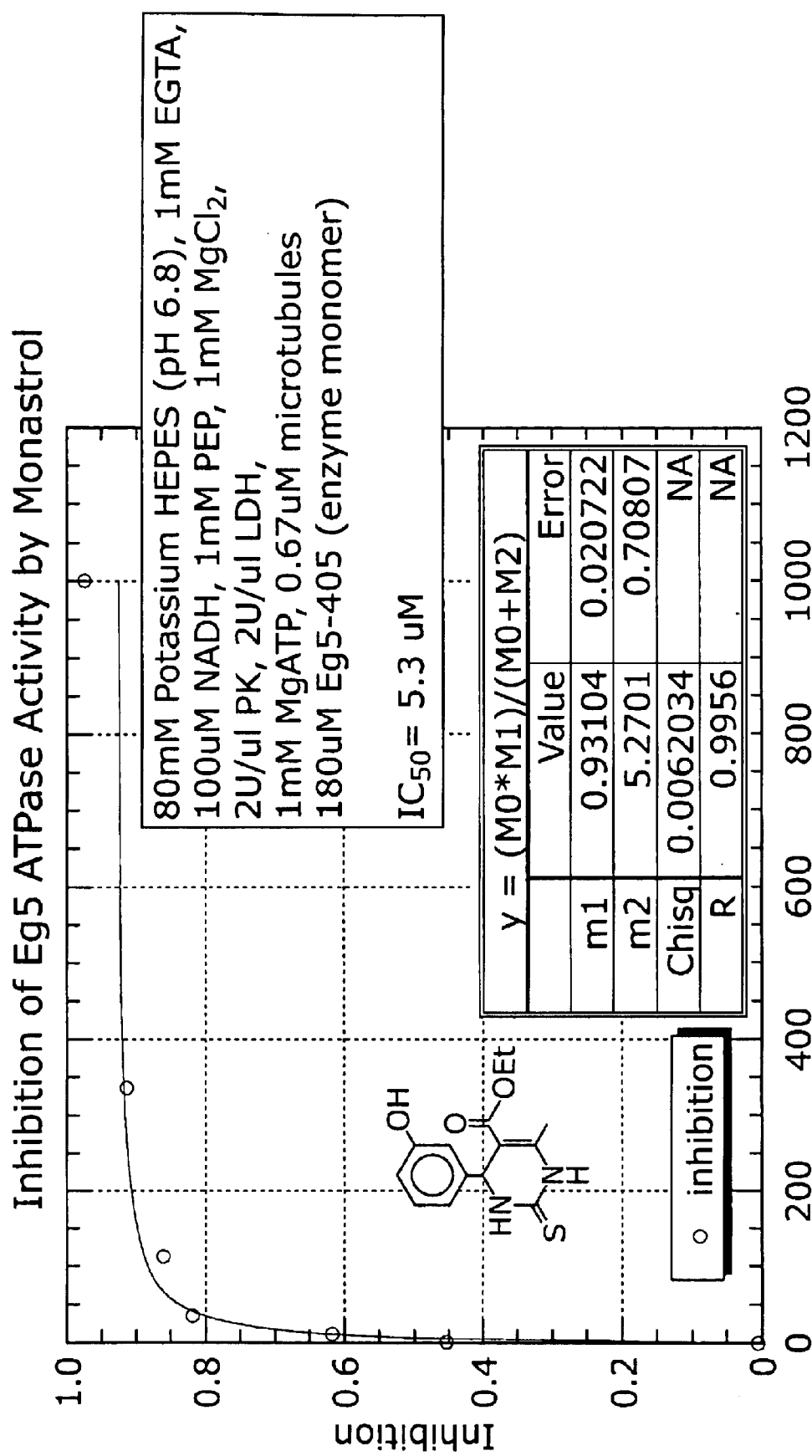
FIG. 9 depicts data from an experiment examining the inhibition of Eg5 ATPase activity by monastrol. As indicated, the IC50 for this experiment is 5.3 uM.

FIGS. 8 and 9 show the inhibition of Eg5 ATPase activity by the beta-carboline 22C16 described by the present invention and by monastrol respectively. Based on these assays, the IC50 for 22C16 equals 1.1 uM. For monastrol, the IC50=5.3 uM. Therefore, based on the ATPase assay described 22C16 is approximately 5 times more potent than monastrol in the inhibition of the ATPase activity of the human kinesin Eg5.

EXAMPLE 3

Synthesis of Monastroline

The synthesis of monastroline (22C16) was performed via the Pictet-Spengler reaction (Ber. 44:2030, 1911; Whaley and Govindachari. *Org. Reaction.* 6:74, 1951; Ungemach et al. *J. Amer. Chem. Soc.* 102:6976–6984, 1980). Recent examples of the use of the Pictet-Spengler reaction are provided by Rousseau and Dodd (*J. Org. Chem.* 63:2731–2737, 1998) and by Leonard et al. (*Tet. Lett.* 38:3071–3074, 1997).

Figure 10:
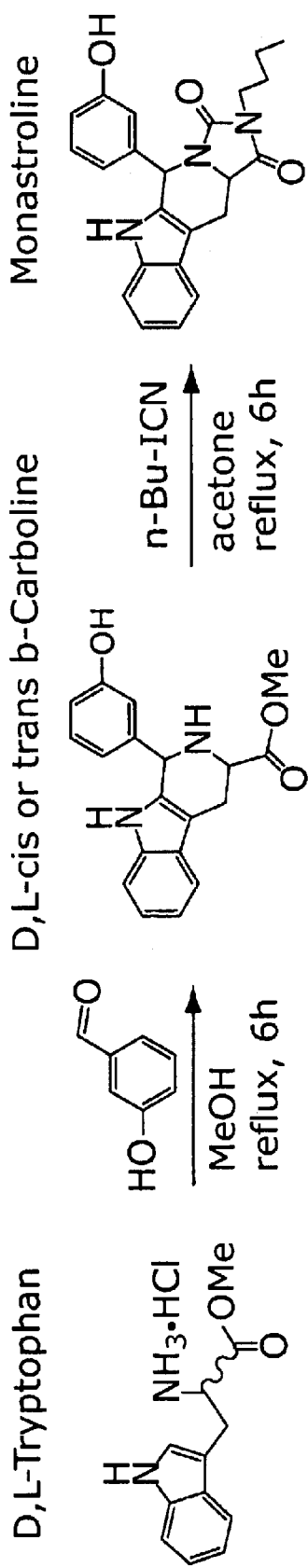
FIG. 10 depicts the synthesis of monastroline.

FIG. 10 depicts the synthetic reaction scheme for monastroline using the Pictet-Spengler reaction. D,L-tryptophan (Sigma-Aldrich) was used as the starting material. D,L-tryptophan was refluxed with 3-hydroxylbenzaldehyde (Sigma-Aldrich) in methanol for approximately 6 hours. The racemic beta-carboline was purified and refluxed with n-BuICN in acetone for approximately 48 hours. Cis and trans isomers of monastroline were separated and purified by standard silica gel chromatography.

EXAMPLE 4

Synthesis of Monastroline Derivatives

Figure 11:
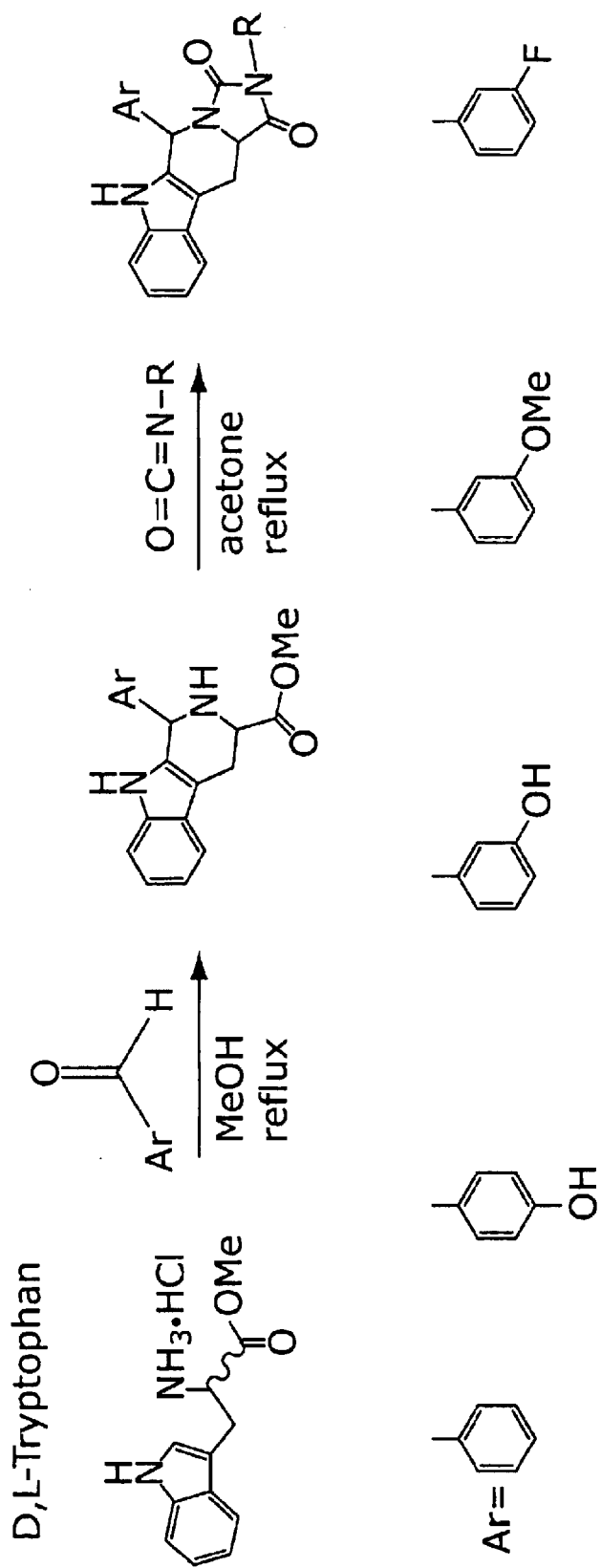
FIG. 11 depicts the synthesis of derivatives of monastroline (Ar=phenyl, p-hydroxyphenyl, m-hydroxyphenyl, m-methoxyphenyl and m-fluorophenyl and R=hydrogen, methyl, ethyl, n-butyl, or α-benzyl). For conjugation of monastroline and derivatives to solid supports R can be $C_n$COOR, where n=1–20, preferably 1, 3, 5, 7, 9, 11 or 13, and wherein R is methyl, ethyl, n-butyl or α-benzyl.

FIG. 11 depicts the synthesis of phenyl derivatives of monastroline which have a structure similar to monastroline and likely have similar biological activity. In FIG. 11, monastroline and derivatives of monastroline may be conjugated to a solid support through the R group wherein R is methyl, ethyl, n-butyl, or alpha-benzyl. Alternatively or additionally, for conjugation to a resin or other solid support, R is $C_nCOOR'$ where n is 1–20, and preferably equal to 1, 3, 5, 7, 9, 11, or 13, and where R' is methyl, ethyl, n-butyl, or alpha-benzyl.

Figure 12:
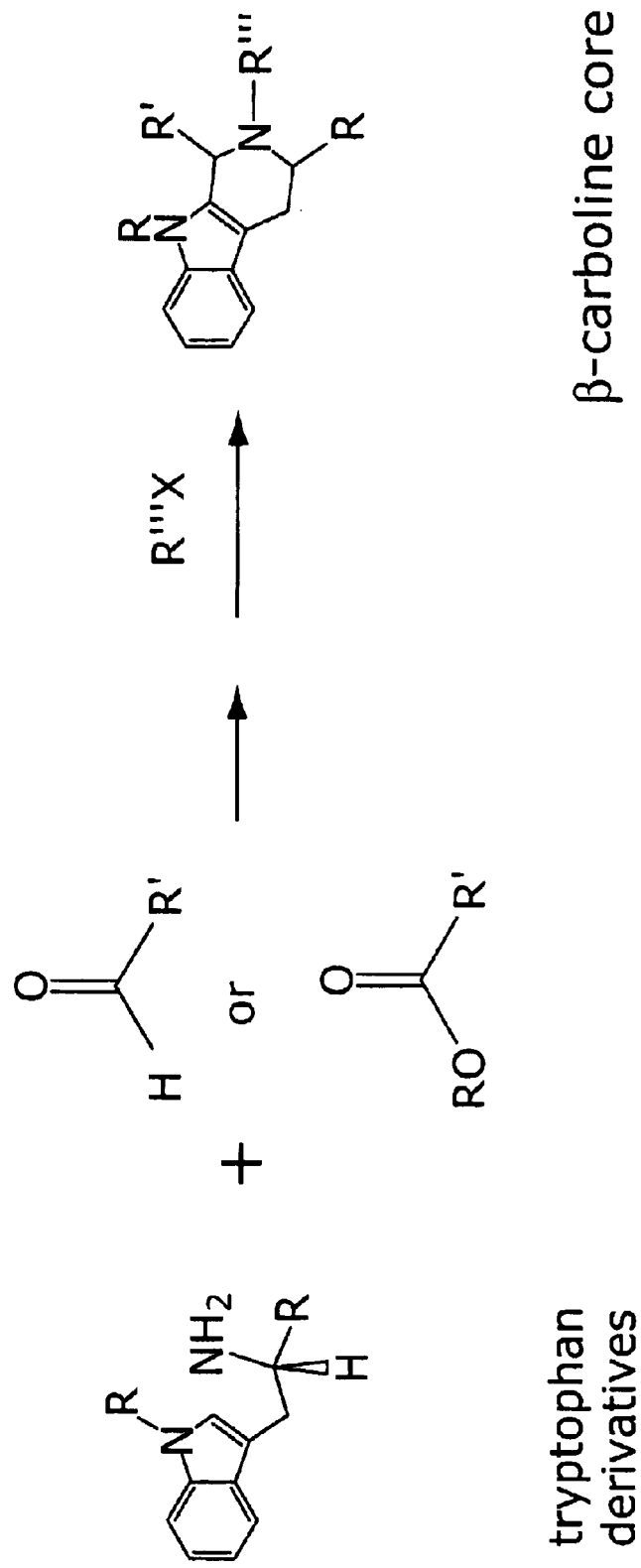
FIG. 12 depicts the synthesis of derivatives the beta-carboline core of monastroline starting with derivatives of tryptophan that are readily available commercially.

The synthesis of beta-carboline derivatives and further modifications of the beta-carboline core of monastroline is depicted in FIG. 12. The synthesis of derivatives having modifications, additions, and combinations thereof to heteroatom functionality is depicted in FIG. 13.

Additionally syntheses of derivatives of monastroline are described herein. The general synthetic scheme is depicted by the following:

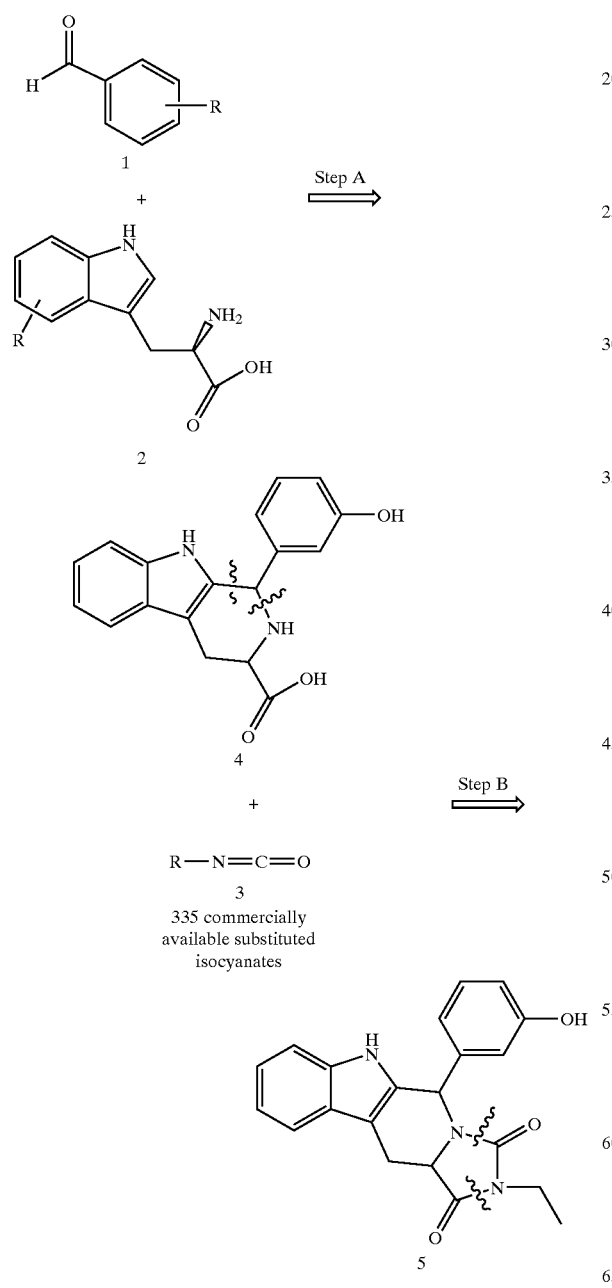

Synthetic reactions involving Step A are readily appreciated by those skilled in the art. A representative reaction is shown below.

Reaction of Tryptophan derivatives (4) with aldehyde building blocks (5).

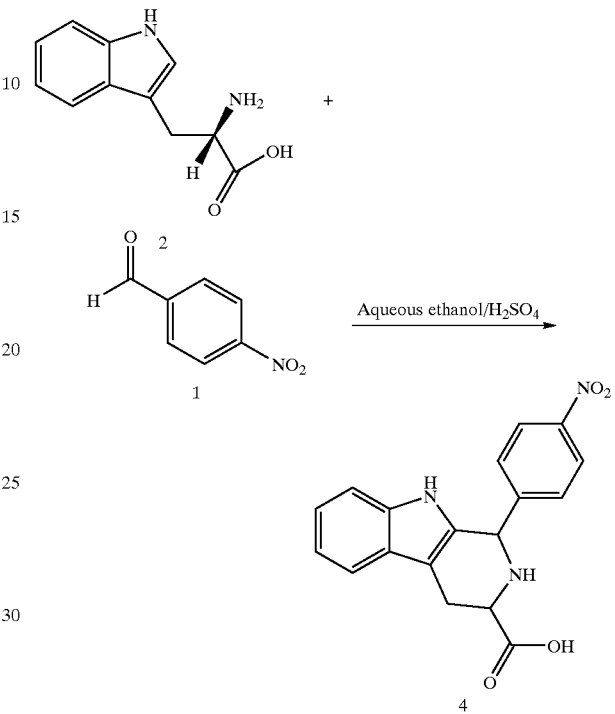

*Journal of the American Chemical Society*, 70:219, 1948

Syntheses of derivatives of monastroline starting with other derivatives of tryptophan are readily appreciated by those skilled in the art. Non-limiting examples are provided below.

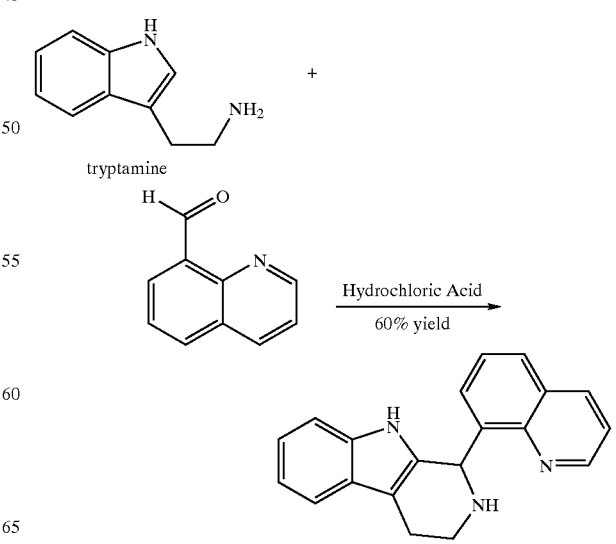

Chem. Nat. Cmpd. 18:598–600, 1982
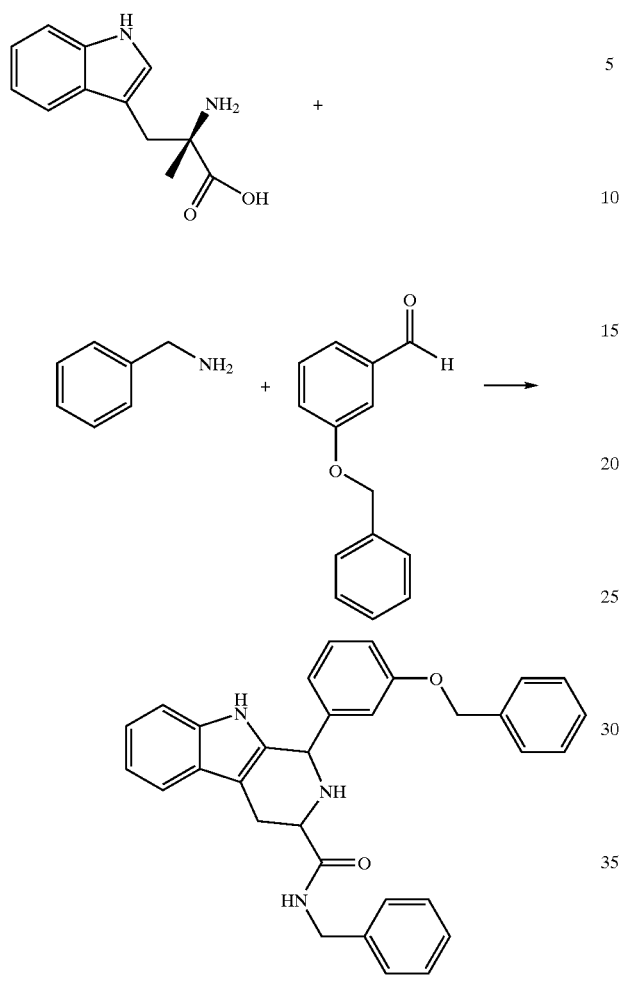
Tetrahedron Lett. 39(11):1291–1294,1998
Non-limiting examples of derivatives of monastroline resulting from the reaction depicted by Step A are provided below. The free acids can be further reacted with an isocynanate. The carboxylic acids can be converted to the amine (*Tetrahedron. Lett.* 39(11):1291–1294, 1998).
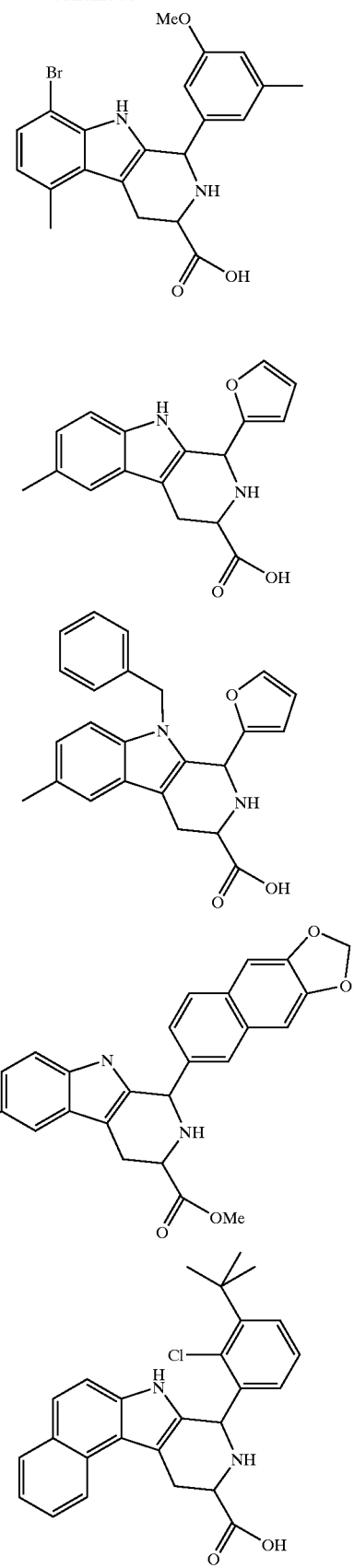

Synth. Commun. 20(12):1793–1810, 1990

Non-limiting examples of derivatives resulting from reactions involving Step B are provided below.

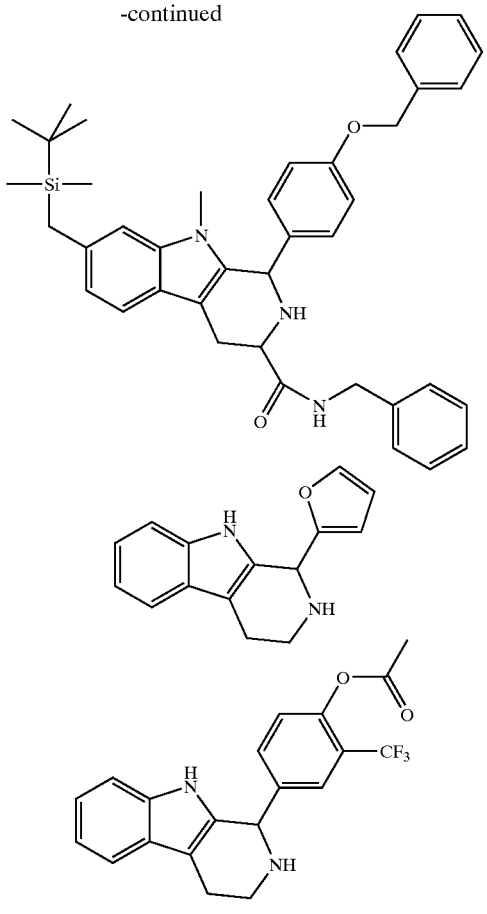

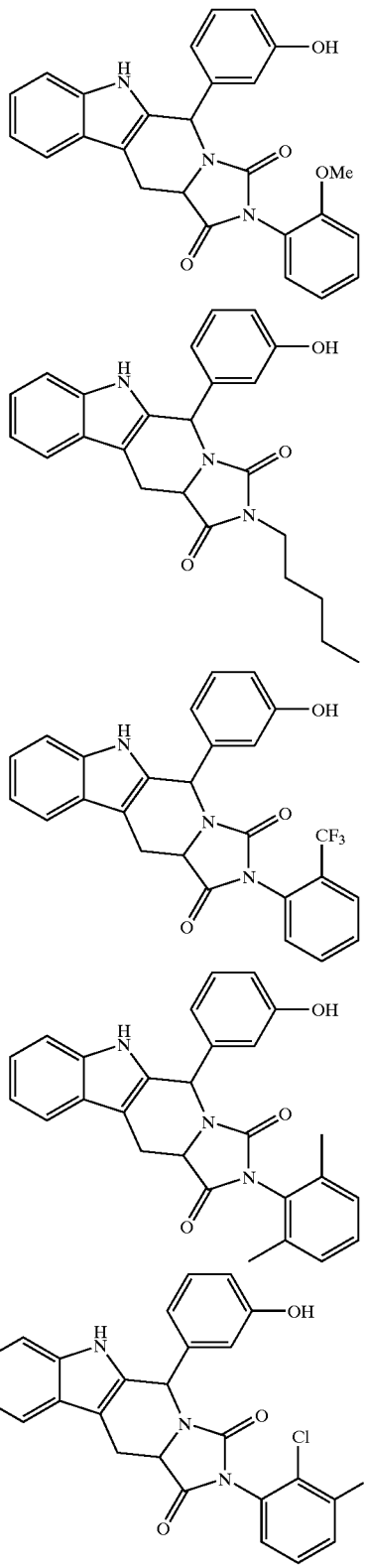

Syntheses involving the reaction depicted in Step B using isocyanates are readily envisioned and appreciated by those skilled in the art. A non-limiting example is provided below to further illustrate reactions involving isocyanate in Step B.

Reaction of beta-carboline 4 with substituted isocyanates (2).

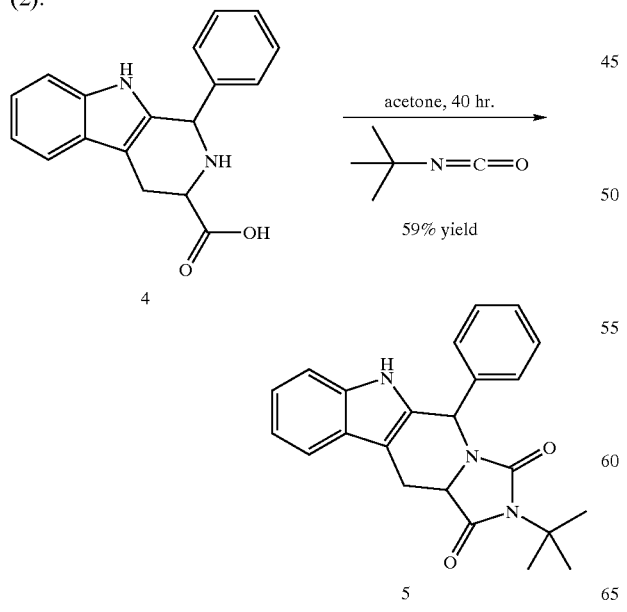

-continued

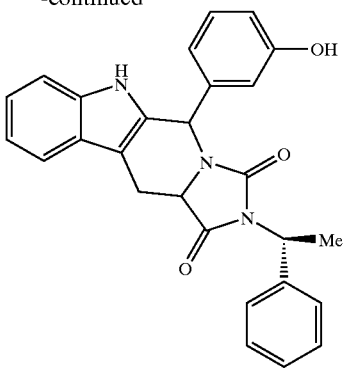

We claim:
1. A compound having the chemical structure:

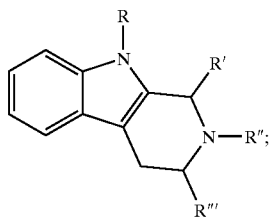

wherein R, R', R" and R'" as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, —(C=O)$R_B$, and —(SO$_2$)$R_B$, wherein each occurrence of $R_B$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and —(C=O)$R_C$, wherein $R_C$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen;
with the proviso that the following groups do not occur simultaneously as defined:
a) R'" is —CO$_2$CH$_3$, and
   (i) R and R" are each hydrogen and R'0 is methyl, ethyl, cyclohexyl, —CH(OEt)$_2$, phenyl, o-nitrophenyl, o-hydroxyphenyl, o-aminophenyl or 3-pyridinyl;
   (ii) R is methyl, R' is methyl, ethyl, cyclohexyl or phenyl, and R" is hydrogen;
   (iii) R is hydrogen, R" is —C(=O)CH$_3$ and R' is propyl or butyl;
   (iv) R' is ethyl and R" is —CH$_2$Ph;
b) R, R' and R'" are each hydrogen, and R" is methyl; and
c) R and R'" are each hydrogen, and R' and R", taken together, are —CH$_2$)$_4$—.

2. A pharmaceutical composition comprising a compound of claim 1 and further comprising a pharmaceutically acceptable carrier.

3. A method of treating an individual having cancerous cells comprising administering to the individual a therapeutically effective amount of a composition comprising a compound having the structure:

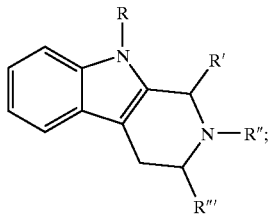

wherein R, R', R" and R'" as valency and stability permit are each independently selected from the group consisting of substituted or unsubstituted, branched or unbranched alkyl, alkenyl, alkynyl, cycloalkyl, cycloalkenyl, cycloalkynyl, aryl, heteroaryl, heterocycle, heteroalkyl, hydrogen, —(C=O)$R_B$, and —(SO$_2$)$R_B$, wherein each occurrence of $R_B$ as valency and stability permit is independently selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, hydrogen, and —(C=O)$R_C$, wherein $R_C$ as valency and stability permit is selected from the group consisting of substituted or unsubstituted, branched or unbranched alkyl, alkenyl, alkynyl, cycloalkyl, cycloalkenyl, cycloalkynyl, aryl, heteroaryl, heteroalkyl, heterocycle, alkoxy, aryloxy, alkylthio, arylthio, heteroaryloxy, heteroarylthio, and hydrogen.

4. The compound of claim 1 wherein R is hydrogen, alkyl, or -alkylaryl; R' is aryl, heteroaryl or heterocycle; R" is hydrogen; and R'" is —(C=O)$R_x$ wherein $R_x$ is OH, alkoxy or —NR$_y$R$_z$, wherein R$_y$ and R$_z$ are independently hydrogen, alkyl or -alkylaryl;
whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

5. The compound of claim 1 wherein R is hydrogen and the compound has the structure:

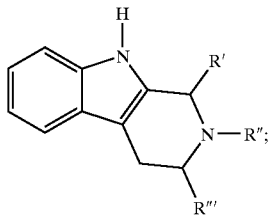

wherein R' is aryl, heteroaryl or heterocycle; R" is hydrogen; and R'" is —(C=O)$R_x$ wherein $R_x$ is OH, alkoxy or —NR$_y$R$_z$, wherein R$_y$ and R$_z$ are independently hydrogen, alkyl or -alkylaryl;
whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

6. The compound of claim 1 wherein R and R" are each hydrogen, R' is aryl or heteroaryl, R'" is —(C=O)OMe and the compound has the following structure:

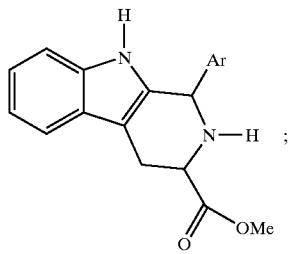

wherein Ar is a substituted or unsubstituted aryl or heteroaryl moiety;

with the proviso that Ar is not phenyl, o-nitrophenyl, o-hydroxyphenyl, o-aminophenyl or 3-pyridinyl.

7. The compound of claim 6 wherein the aryl moiety is $_m$-hydoxyphenyl, $_p$-hydroxyphenyl, $_m$-fluorophenyl or $_m$-methoxyphenyl.

8. The compound of claim 7 wherein the aryl moiety is m-hydroxyphenyl and the compound has the structure:

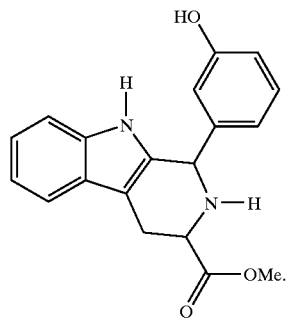

9. The composition of claim 2 wherein R is hydrogen, alkyl, or -alkylaryl; R' is aryl, heteroaryl or heterocycle; R" is hydrogen; and R'" is —(C=O)$R_x$ wherein $R_x$ is OH, alkoxy or —N$R_y$$R_z$, wherein $R_y$ and $R_z$ are independently hydrogen, alkyl or -alkylaryl;

whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

10. The composition of claim 2 wherein R is hydrogen and the compound has the structure:

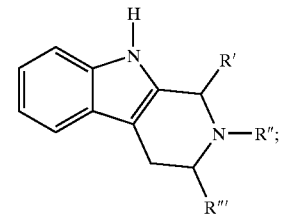

wherein R' is aryl, heteroaryl or heterocycle; R" is hydrogen; and R'" is —(C=O)$R_x$ wherein $R_x$ is OH, alkoxy or —N$R_y$$R_z$, wherein $R_y$ and $R_z$ are independently hydrogen, alkyl or -alkylaryl;

whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

11. The composition of claim 2 wherein R and R" are each hydrogen, R' is aryl or heteroaryl, R'" is —(C=O)OMe and the compound has the following structure:

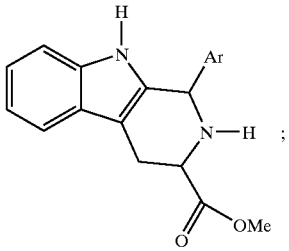

wherein Ar is a substituted or unsubstituted aryl or heteroaryl moiety;

with the proviso that Ar is not phenyl, o-nitrophenyl, o-hydroxyphenyl, o-aminophenyl or 3-pyridinyl.

12. The composition of claim 11 wherein the aryl moiety is $_m$-hydoxyphenyl, $_p$-hydroxyphenyl, $_m$-fluorophenyl or $_m$-methoxyphenyl.

13. The composition of claim 12 wherein the aryl moiety is m-hydroxyphenyl and the compound has the structure:

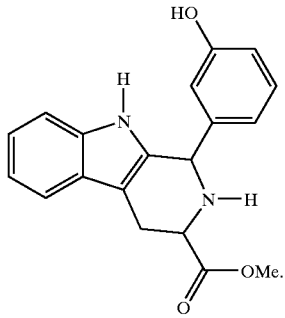

14. The method of claim 3 wherein, in the compound, the following groups do not occur simultaneously as defined:
   a) R'" is —CO$_2$CH$_3$, and
      (i) R and R" are each hydrogen and R' is methyl, ethyl, cyclohexyl, —CH(OEt)$_2$, phenyl, o-nitrophenyl, o-hydroxyphenyl, o-aminophenyl or 3-pyridinyl;
      (ii) R is methyl, R' is methyl, ethyl, cyclohexyl or phenyl, and R" is hydrogen;
      (iii) R is hydrogen, R" is —C(=O)CH$_3$ and R' is propyl or butyl;
      (iv) R' is ethyl and R" is —CH$_2$Ph;
   b) R, R' and R'" are each hydrogen, and R" is methyl; and
   c) R and R'" are each hydrogen, and R' and R", taken together, are —(CH$_2$)$_4$—.

15. The method of claim 3 wherein, in the compound, R is hydrogen, alkyl, or —alkylaryl; R' is aryl, heteroaryl or heterocycle; R" is hydrogen; and R'" is —(C=O)$R_x$ wherein $R_x$ is OH, alkoxy or —N$R_y$$R_z$, wherein $R_y$ and $R_z$ are independently hydrogen, alkyl or -alkylaryl;

whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

16. The method of claim 3 wherein, in the compound, R is hydrogen and the compound has the structure:

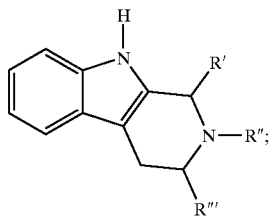

wherein R' is aryl, heteroaryl or heterocycle; R" is hydrogen; and R'" is —(C=O)$R_x$ wherein $R_x$ is OH, alkoxy or —$NR_yR_z$, wherein $R_y$ and $R_z$ are independently hydrogen, alkyl or -alkylaryl;

whereby each of the foregoing alkyl and alkoxy moieties may be independently substituted or unsubtituted, linear or branched or cyclic or acyclic; and each of the foregoing aryl, -alkylaryl, heteroaryl and heterocycle moieties may be independently substituted or unsubstituted.

17. The method of claim 3 wherein, in the compound, R and R" are each hydrogen, R' is aryl or heteroaryl, R'" is —(C=O)OMe and the compound has the following structure:

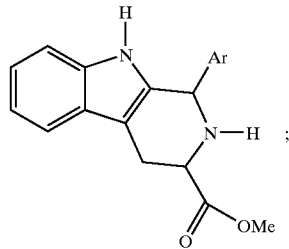

wherein Ar is a substituted or unsubstituted aryl or heteroaryl moiety.

18. The method of claim 17 wherein, in the compound, the aryl moiety is m-hydroxyphenyl, p-hydroxyphenyl, m-fluorophenyl or m-methoxyphenyl.

19. The method of claim 18 wherein, in the compound, the aryl moiety is m-hydroxyphenyl and the compound has the structure:

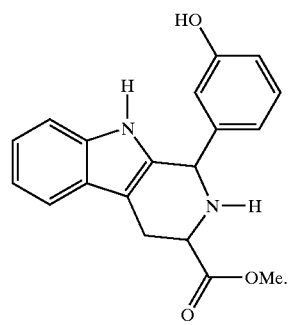

* * * * *